United States Patent
Collazo et al.

(10) Patent No.: US 9,387,300 B2
(45) Date of Patent: Jul. 12, 2016

(54) ADJUSTABLE NASAL PRONG AND HEADGEAR ASSEMBLY

(75) Inventors: Louis Javier Collazo, Pompano Beach, FL (US); Sanjay Chandran, Boca Raton, FL (US); Norman Hansen, Highland Beach, FL (US)

(73) Assignee: RESPCARE, INC., Coconut Creek, FL (US)

( * ) Notice: Subject to any disclaimer, the term of this patent is extended or adjusted under 35 U.S.C. 154(b) by 259 days.

(21) Appl. No.: 12/731,803

(22) Filed: Mar. 25, 2010

(65) Prior Publication Data

US 2011/0232649 A1    Sep. 29, 2011

(51) Int. Cl.
 *A61M 16/06* (2006.01)
 *A61M 16/08* (2006.01)
 A61M 15/08 (2006.01)
 A62B 7/00 (2006.01)

(52) U.S. Cl.
 CPC ............ *A61M 16/06* (2013.01); *A61M 16/0666* (2013.01); *A61M 16/0683* (2013.01); *A61M 16/0816* (2013.01); *A61M 16/0825* (2014.02); *A61M 2205/42* (2013.01)

(58) Field of Classification Search
 CPC ............ A61M 16/0683; A61M 16/0666; A61M 16/0816; A61M 16/0638; A61M 16/06; A61M 16/0825; A61M 2205/42
 USPC ............ 128/206.11, 207.18, 205.25, 207.13, 128/206.24, 207.11, 200.24, 201.22, 128/202.27, 203.29, 204.18, 206.21, 128/206.26, 206.28, 207.17
 See application file for complete search history.

(56) References Cited

U.S. PATENT DOCUMENTS

| | | | |
|---|---|---|---|
| 5,724,965 A | 3/1998 | Handke et al. | |
| 6,431,172 B1 | 8/2002 | Bordewick | |
| 7,255,107 B1 * | 8/2007 | Gomez | A61M 16/0666 128/206.11 |
| 7,318,437 B2 * | 1/2008 | Gunaratnam et al. | 128/206.11 |
| 2002/0096178 A1 * | 7/2002 | Ziaee | 128/207.18 |
| 2005/0072428 A1 * | 4/2005 | Ho | A61M 16/06 128/205.25 |
| 2006/0032504 A1 * | 2/2006 | Burton et al. | 128/207.11 |
| 2006/0124131 A1 | 6/2006 | Chandran et al. | |
| 2006/0174887 A1 | 8/2006 | Chandran et al. | |
| 2006/0283461 A1 * | 12/2006 | Lubke et al. | 128/207.11 |
| 2007/0272249 A1 | 11/2007 | Chandran et al. | |
| 2008/0011305 A1 | 1/2008 | Chandran et al. | |
| 2008/0190432 A1 * | 8/2008 | Blochlinger et al. | 128/205.25 |
| 2009/0188507 A1 * | 7/2009 | LaCava | 128/207.13 |
| 2010/0229868 A1 * | 9/2010 | Rummery et al. | 128/205.25 |
| 2010/0319689 A1 * | 12/2010 | Kwok et al. | 128/202.13 |

* cited by examiner

*Primary Examiner* — Tan-Uyen (Jackie) T Ho
*Assistant Examiner* — Mark Wardas
(74) *Attorney, Agent, or Firm* — Allen Dyer Doppelt Milbrath & Gilchrist

(57) ABSTRACT

The invention is directed to a ventilation interface, which includes a cannula having one or more nasal prongs, a ventilation tube connected to the cannula and headgear. The cannula is secured onto the patient through one or more arced couplers positioned between the cannula and headgear. The cannula has a first side wall, a second side wall and a top wall which form a reservoir. The top wall includes a first portion, a second portion and a notch positioned between the first portion and second portion. The ventilation tube includes one or more bleed ports and provides breathable gas to a patient. The headgear includes a first strap and a second strap. The first strap includes a first portion and second portion that contains two or more slots to connect the second strap. Each portion of the first strap includes an inner layer and an outer layer.

14 Claims, 19 Drawing Sheets

ADJUSTABLE NASAL PRONG AND HEADGEAR ASSEMBLY

FIELD OF THE INVENTION

This invention is directed to nasal prong and headgear assemblies for use when delivering breathable gas in treating various respiratory issues including, but not limited to, sleep apnea and in other forms of assisted respiration. More specifically, the invention relates to a headgear capable of pivotally attaching with the cannula of the nasal prong through one or more arced couplers.

BACKGROUND OF THE INVENTION

Ventilation interfaces are used for various applications. One such application involves current treatments for sleep apnea. Sleep apnea is a common sleep disorder characterized by sustained pauses in breathing during sleep. The disorder occurs in both infants and adults. Each episode, known as an apnea, can last more than ten seconds and results in blood oxygen desaturation. A clinical diagnosis of sleep apnea is defined as five or more episodes per hour. There are three types of sleep apnea: central, obstructive, and complex.

Obstructive sleep apnea (OSA) constitutes the most common form of sleep apnea. OSA is a medical condition that includes repeated, prolonged episodes of cessation of breathing during sleep. During a period of wakefulness, the muscles of the upper part of the throat passage of an individual keep the passage open, thereby permitting an adequate amount of air (which contains oxygen) to flow to the lungs. During sleep, the throat passage narrows due to relaxation of the muscles. In individuals having a normal sized throat passage, the narrowed throat passage remains open enough to permit a sufficient level of oxygen to flow into the lungs. However, in individuals with smaller sized throat passages, the narrowed throat passage prohibits adequate amounts of oxygen to flow into the lungs.

In addition, an obstruction, such as a relatively large tongue, an occlusion in the upper respiratory track or an odd-shaped plate can also prohibit a sufficient amount of oxygen to flow to the lungs—thus also resulting in OSA. OSA can result in a variety of medical conditions including daytime drowsiness, headache, weight gain or loss, limited attention span, memory loss, poor judgment, personality changes, lethargy, inability to maintain concentration and/or depression.

Other medical conditions can also prevent individuals, including adults and infants, from receiving an adequate amount of oxygen to the lungs. For example, an infant who is born prematurely can have lungs that are not developed to an extent necessary to receive adequate amounts of oxygen. Further, prior to, during, and/or subsequent to certain medical procedures and/or medical treatments, an individual can be unable to receive an adequate amount of oxygen. Under these circumstances, it is known to use a ventilation interface to apply a positive pressure to the throat of the individual, thereby permitting an adequate amount of oxygen to flow into the lungs.

In known ventilation interfaces, oxygen and/or room air containing oxygen is delivered through the mouth and/or nose of the individual. The most common form of positive pressure treatment for OSA is use of a continuous positive airway pressure (CPAP) device. A CPAP device forces a pressurized breathable gas into the patient's respiratory track and allows air to pass the obstruction(s) and/or occlusion(s). Other forms of positive pressure delivery exist, such as bi-Level positive airway pressure (BiPAP) in which a relatively higher positive pressure is maintained during inspiration and a relatively lower positive pressure is maintained during expiration, and intermittent mechanical positive pressure ventilation (IPPV) in which a positive pressure is applied when apnea is sensed (i.e., the positive airway pressure is applied intermittently or non-continuously). With all these types of therapy, a positive pressure device (i.e., flow generator) connects via a ventilation tube to a ventilation interface. The interface connects to either the patient's nose, mouth or both orifices.

Various interfaces have been developed for positive pressure, and more specifically CPAP therapy. These include various shaped full-face masks, nasal masks, nasal prong masks, oral masks and hybrid masks (i.e., those masks that combine masks such as having an oral cavity with nasal prongs). Nasal prongs offer one popular form of interface for use with CPAP therapy because they are relatively small, less bulky and more comfortable for many patients to wear for long periods of time.

Nasal prongs can generally be separated into two types: nasal pillows and nasal inserts. Nasal pillows typically abut against the openings of a user's nares when in use and may not be inserted substantially within the nasal passages. Nasal inserts are typically positioned within the nasal passages of a user and may or may not abut against the nasal openings. Embodiments and the principles thereof are contemplated for any nasal prong and the like, as will be readily recognized by one having ordinary skill in the art. Nevertheless, for illustrative purposes in a non-limiting manner, exemplary embodiments are described below in reference to nasal pillows.

A seal is maintained between the patient and the ventilation interface through use of headgear. More specifically, the headgear of a nasal pillow assembly creates an upward force by compressing the nasal pillows onto the nasal openings. This compression should be sufficient to effectuate the seal without creating discomfort to the patient. These nasal pillow systems, unlike nasal mask and full-face mask interfaces, help reduce the risk of patients feeling claustrophobic while being treated for OSA through CPAP therapy. However, one issue with nasal pillows is that they have to be calibrated and properly fitted to maintain an effective seal between the interface and patient, while still being comfortable to wear for long periods of time.

Various forms of nasal pillow and headgear assemblies have been developed which attempt to address these design criteria. Two initial examples of nasal pillow interfaces found in the prior art include U.S. Pat. Nos. 5,724,965 and 6,431,172. Both nasal pillow systems require multiple part construction for the reservoir that includes both a hard plastic first component and a softer second component. Thus, the gas reservoir requires at least two parts, which leads to various connecting points that can leak. Moreover, both these prior art systems require complicated headgear, which increases the risk of the patient feeling claustrophobic. Moreover, these designs are complicated, difficult to calibrate and fail to allow easy adjustment by the patient during use.

While more recent commercially available nasal pillow designs continue to provide alternative headgear and connection systems to calibrate the reservoir proximate to the patient's face, these systems still have several drawbacks. Two such examples are the ResMed® Swift LT and the Fisher & Paykel® Opus™ nasal pillows. Both require a two part cannula comprised of: a rigid frame that connects with the ventilation tube and a second more pliable silicone base that has the nasal pillows.

The Swift LT interface includes a ratchet system, which can rotate and lock at various positions relative to the headgear to adjust the angle of the nasal pillows to the patient's face. Since the axis of the ratchet system is well below the nasal pillows, the nasal pillows move in an arc relative to the axis. Therefore, any rotational adjustment undesirably impacts how the user wears the headgear, and consequently forces the user to recalibrate and make further adjustments to the interface and headgear to achieve a proper fit. Also, the toothed part of the ratchet system (which connects to the reservoir) is made of a soft rubber or silicone elastomer, which invariably will degrade and lead to stripping—thus inhibiting the ability to angle the pillows relative to the headgear and effectuate an effective seal between the nares and the patient. Moreover, the complicated design requires a significant level of time and attention to adjust.

The Opus™ nasal pillow does not include a means at all to adjust the angle of the pillows relative to the headgear and therefore the user's face. There are several other drawbacks to both the ResMed® Swift LT and the Fisher & Paykel® Opus™ nasal pillows. Neither product allows the user to quickly disconnect the cannula or to disconnect the cannula while maintaining the headgear in place. Also, both products require extra parts to provide the adequate pillow sizes required to fit different patients.

Accordingly, there is a need in the art of ventilation interfaces for a nasal prong that allows for more simplified construction and that includes an effective means for adjusting and calibrating the interface in relation to the patient to ensure long term comfort. In addition, there is a need in the art for an improved headgear that can connect to the interface to allow a patient to easily assemble, disassemble, adjust and position the interface to ensure an effective seal with the nares. Finally, there is a need in the art to simplify the nasal prong offerings without compromising sealing and comfort. In short, the design should allow more comfortable long term use, require less assembly and be easily calibrated.

SUMMARY OF THE INVENTION

The present invention solves many of the problems with current ventilation interfaces, including nasal prong and headgear designs. In one embodiment of the invention, the ventilation interface may include a single-body constructed cannula made of silicone elastomer having a first side wall, a corresponding second side wall in parallel relation to the first side wall, a top wall, a front wall and a back wall which form a reservoir. The top wall of the cannula may include a first portion, a second portion and a notch positioned between both portions. Integrally attached to both portions is a set of two nasal prongs, the first nasal prong positioned on the first portion while the second nasal prong is located on the second portion of the cannula. Connected to the cannula through a ball-and-socket connector is a ventilation tube capable of providing pressurized breathable gas to a patient. Positioned between the ball-and-socket connector and the ventilation tube is a connector that contains one or more bleed ports.

Headgear may be attached to the cannula through two arced couplers. A first arced coupler includes a curved female sleeve located on the first side wall of the cannula and a corresponding first curved male tine attached to the headgear. Similarly, a second arced coupler includes a curved female sleeve located on the second side wall of the cannula and a second curved male tine which is also attached to the headgear.

The invention is further directed to an improved headgear that may comprise a first strap and a corresponding second strap. The first strap includes a first portion and a second portion, the second portion mirroring the size and orientation of the first portion. Each portion of the first strap may include a flexible inner layer and corresponding rigid outer layer. Each inner layer has a first section, a second section and a corresponding third section of material. The inner layer may be made of single piece construction.

The second section of the flexible inner layer is oriented at an angle below the first section, while the third section is oriented at an angle above the second portion. The third section connects to the cannula through the arced coupler. The outer layer has one or more slots. Optionally, the shape and configuration of the outer layer mirrors that of the inner layer. More specifically, the outer layer includes a first slot and a corresponding second slot, the second slot having a position and angle different than the first slot such that both slots are capable of positioning the second strap at a different angle about a patient's head.

The second strap of the headgear includes a first end and a corresponding second end, both ends having a hook-and-loop fastener sufficient to attach the second strap to one or more slots located on the outer layer of the first strap. A tube holder is positioned on the middle portion of the second strap. This tube holder has a sufficient size and dimension to maintain and secure the ventilation tube.

In another embodiment of the invention, the headgear may attach to the cannula through a male member and female slot system—instead of a sleeve and tine assembly. More specifically, the arced coupler may include a male member located on a side wall of the cannula. The male member has a sufficient size and dimension to as to fit within and pivotally engage a female slot located on the headgear. Moreover the unique shape of the arced coupler allows the user to pivot the cannula about an axis to properly seat the ventilation interface proximate to the nares to effectuate an improved seal.

In yet another embodiment of the invention, the headgear may engage the cannula through a pin and receptacle configuration. More specifically, the back wall of the cannula includes a receptacle. In addition, the headgear may include a rigid pivot pin. The pin has a sufficient size and dimension to rest within and engage the receptacle.

In still yet another embodiment of the invention, the headgear may attach to the cannula of the ventilation interface through at least one connecting portion, which includes a center strap.

In addition, nasal prongs may also be detachably coupled with the ventilation interface. Each detachable nasal prong includes at least two prong portions. The prong portions offer the patient different sizes or styles of nasal prongs in one component. In addition (or alternatively), the nasal prongs can have an upper portion that is located at the distal tip of the nasal prong. The upper portion is adjustable to different configurations.

BRIEF DESCRIPTION OF THE DRAWINGS

For a fuller understanding of the invention, reference is made to the following detailed description, taken in connection with the accompanying drawings illustrating various embodiments of the present invention, in which.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. The terms "embodiment of the invention," "embodiments", or "invention" do not require that all embodiments of the invention include the discussed feature, advantage, or mode of operation.

The invention described in detail below and in the figures is designed to cooperate and be used with any form of ventilation interface for the administration of breathable gas having a headgear and some form of facial seal. Such ventilation interfaces can include any form of facial mask, nasal prong mask, so called "hybrid" masks or other style and shaped masks having an oral cavity and some form of nasal prong— which will be readily understood by those of ordinary skill in the art. Accordingly, the ventilation interfaces described and disclosed in United States Patent Application Nos. 2006/10124131 (Chandran et al.), 2006/0174887 (Chandran et al.), 2007/10272249 (Chandran et al.), and 2008/0011305 (Chandran et al.) are incorporated by reference herein in their entireties.

Nasal prongs can generally be separated into two types: nasal pillows and nasal inserts. Nasal pillows typically abut against the openings of a user's nares when in use and may not be inserted substantially within the nasal passages. Nasal inserts are typically positioned within the nasal passages of a user and may or may not abut against the nasal openings. Embodiments and the principles thereof are contemplated for any nasal prong and the like, as will be readily recognized by one having ordinary skill in the art. Nevertheless, for illustrative purposes in a non-limiting manner, exemplary embodiments are described below in reference to nasal pillows.

The Overall Ventilation Interface

Figure 1:
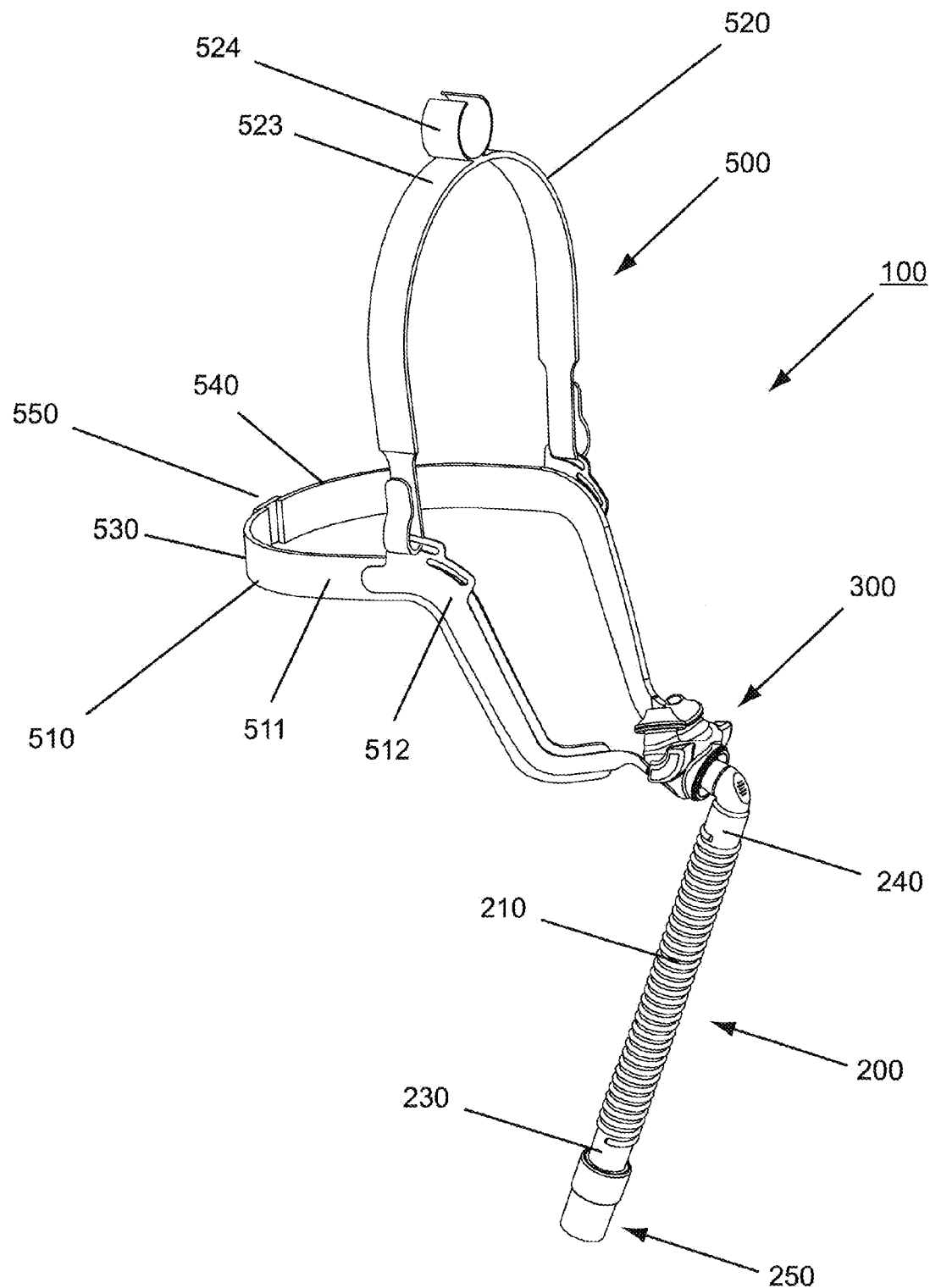
FIG. 1 is a perspective view of the cannula and headgear assembly.
Figure 2:
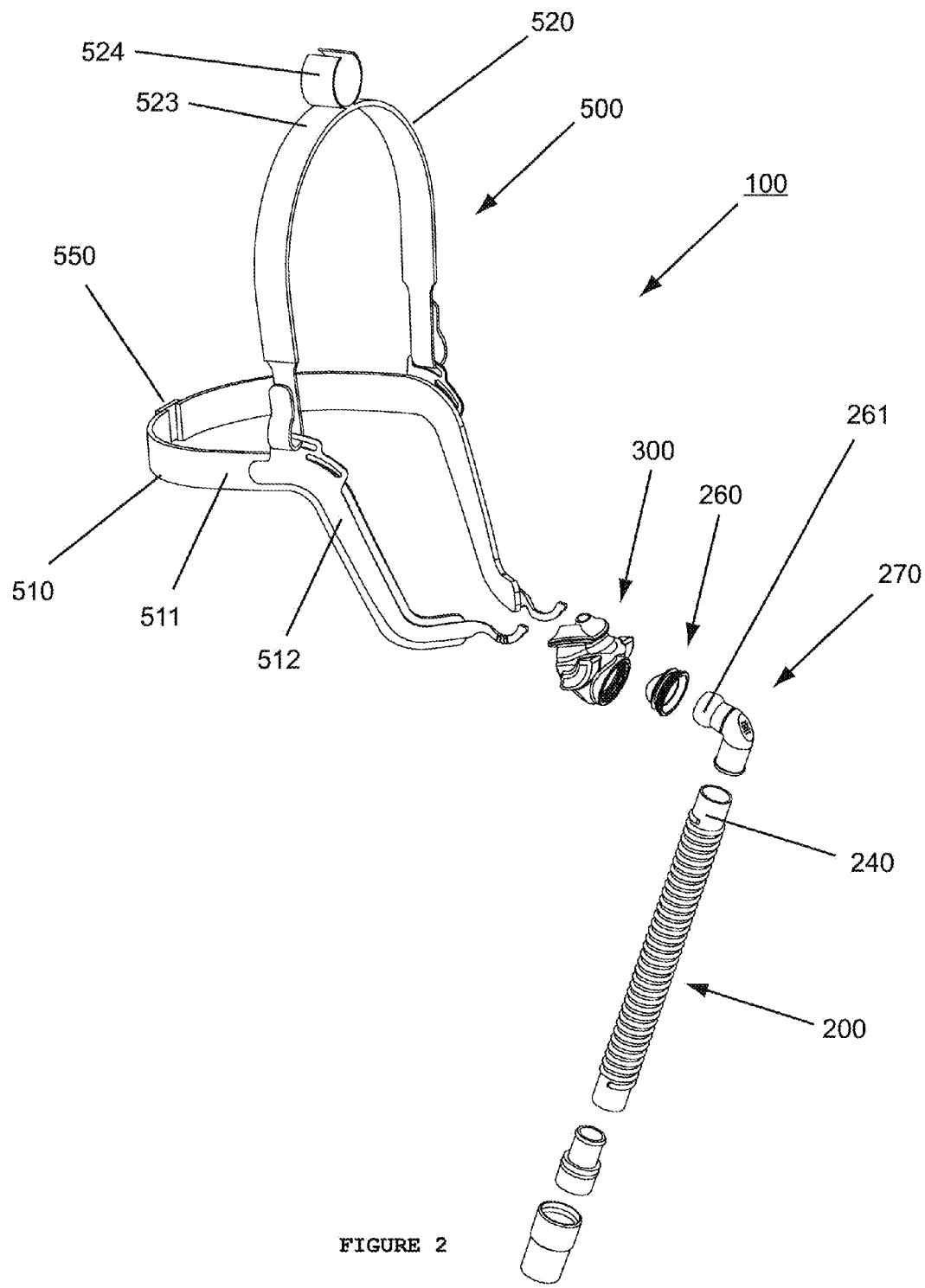
FIG. 2 is an exploded view of the various components of the cannula and headgear assembly.

One embodiment of the invention includes a ventilation interface 100 illustrated in FIGS. 1 and 2. First turning to FIG. 1, the interface 100 is comprised of three components: a ventilation Lube 200, a cannula 300 and headgear 500. Preferably made of a polymer or composite, the ventilation tube 200 is soft, bendable and flexible. The ventilation tube 200 contains a plurality of circular ridges 210 (in parallel relationship to one another) which helps ensure the ventilation tube 200 does not kink or become bent so as to reduce the pressure of supplied breathable gas. In other embodiments, the ridges 210 could be helically swept over at least a portion of the length of the ventilation tube 200.

The ventilation tube 200 includes a first end 230 and a corresponding second end 240. Located at the first end 230 of the ventilation tube 200 is a rigid fitting 250, typically made of hard plastic, which allows connection to the flow generator (not shown). Rigid fitting 250 preferably is a swivel coupling, comprised of at least two parts. The second end 240 of the ventilation tube 200 connects with the cannula 300. In embodiments, the ventilation interface 100 may have more than one ventilation tube 200 and the rigid fitting may be in the form of a "Y" coupler.

FIG. 1 further illustrates the salient components of the headgear 500 (discussed in detail below). As shown, the headgear 500 includes a first strap 510 and a second strap 520. The first strap 510 includes an inner layer 511 and an outer layer 512. The outer layer 512 extends throughout at least a portion of the inner layer 511 of the first strap 510. The inner layer 511 should be flexible and made of a compressible and bendable material, which can include, but is not limited to, neoprene. Other similar material known to those of ordinary skill in the art can also be used. The outer layer 512 is preferably more rigid than the inner layer 511, but should still be flexible to allow conformance to the curvature of the patient's face (not shown). The outer layer 512 of the first strap 510 is preferably made of a polymer, thin flexible metal, or composite.

The first strap 510 of the headgear 500 includes a first portion 530 and a corresponding second portion 540. The first portion 530 connects to the second portion 540 through connector 550. The connector 550 allows for adjustment (i.e., loosening and tightening) of both the first portion 530 and second portion 540 onto the face. The connector 550 is preferably plastic and capable of maintaining both portions 530 and 540 in a compressed state on the patient's face.

FIG. 1 also illustrates the second strap 520 of the headgear 500. The second strap 520, like the inner layer 511 of the first strap 510, is soft, flexible and preferably includes neoprene. The second strap 520 has a middle portion 523. Positioned on the middle portion 523 of the second strap 520 is a tube holder 524. The tube holder 524 is of sufficient size and dimension so as to hold and maintain the ventilation tube 200 while the interface 100 is worn by the patient.

The tube holder 524 may be constructed of a polymer that allows the ventilation tube 200 to fit or snap into it. The tube holder 524 may also be formed of a material that allows it to wrap around and hold the ventilation tube 200, such as fabric with hook and loop closure ends. In embodiments, the tube holder 524 may be located on any portion of the headgear 500 to allow the patient to route the ventilation tube 200 in different positions.

As shown in FIGS. 1 and 2, the cannula 300 is connected to the ventilation tube 200. While there exist a variety of means by which the ventilation tube 200 can connect to the cannula 300, one preferred embodiment of the ventilation interface 100 includes a connector 270 located on the second end 240 of the ventilation tube 200. As shown, one form of connector 270 contemplated by the invention is a ball-and-socket connector. Such embodiment would allow connector 270 to have three degrees of freedom with the cannula 300 to allow a large degree of roll, pitch and yaw. Other embodiments contemplate having the connector 270 and cannula 300 couple as a swivel to allow 360 degrees of rotation and one degree of freedom.

As illustrated in FIG. 1 and FIG. 2, a socket 260 is located between the cannula 300 and connector 270. Such connector 270 has a ball 261 on the distal end that engages the socket 260. Such ball 261 and socket 260 are preferably made of hard plastic. The various degrees of freedom allow the ventilation tube 200 to be positioned below, along, or above the patient's face.

While the connector 270 shown in FIG. 2 is "L" shaped akin to an elbow, other alternative shaped can be used and employed within the ventilation interface 100. This connector 270 also includes one or more bleed ports 280 (as further shown in FIG. 3C) of sufficient size and dimension to allow the patient to exhale the breathable gas supplied by a flow generator. The bleed ports 280 can be a plurality of holes 281 oriented within the connector 270 to minimize noise while dispersing the expelled air. However, in other embodiments contemplated by the invention, these bleed ports 280 can be located on other portions of the ventilation interface 100 including, but no way limited to, the cannula 300.

Figure 3A:
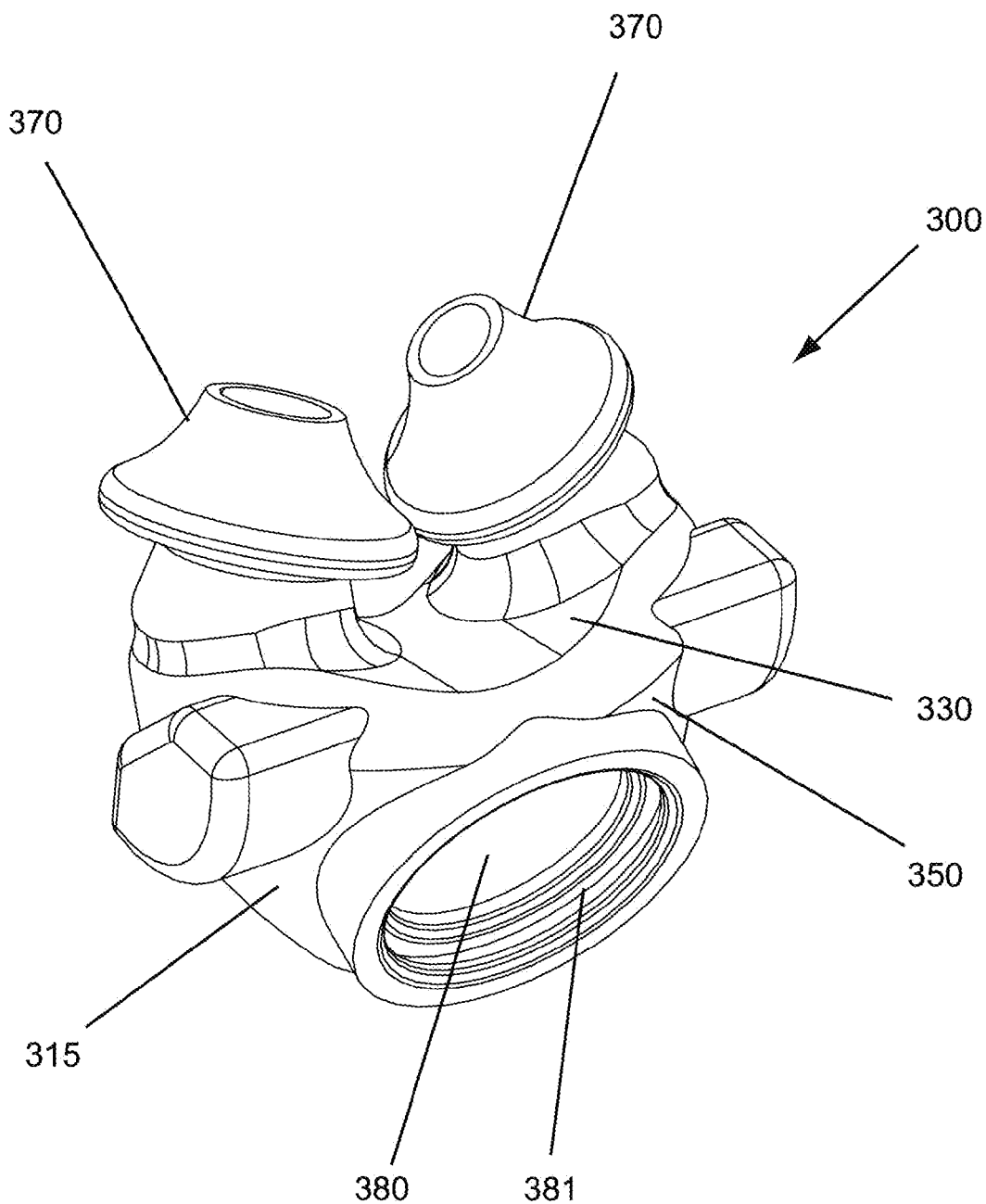
FIG. 3A is a front perspective view of the cannula.
Figure 3B:
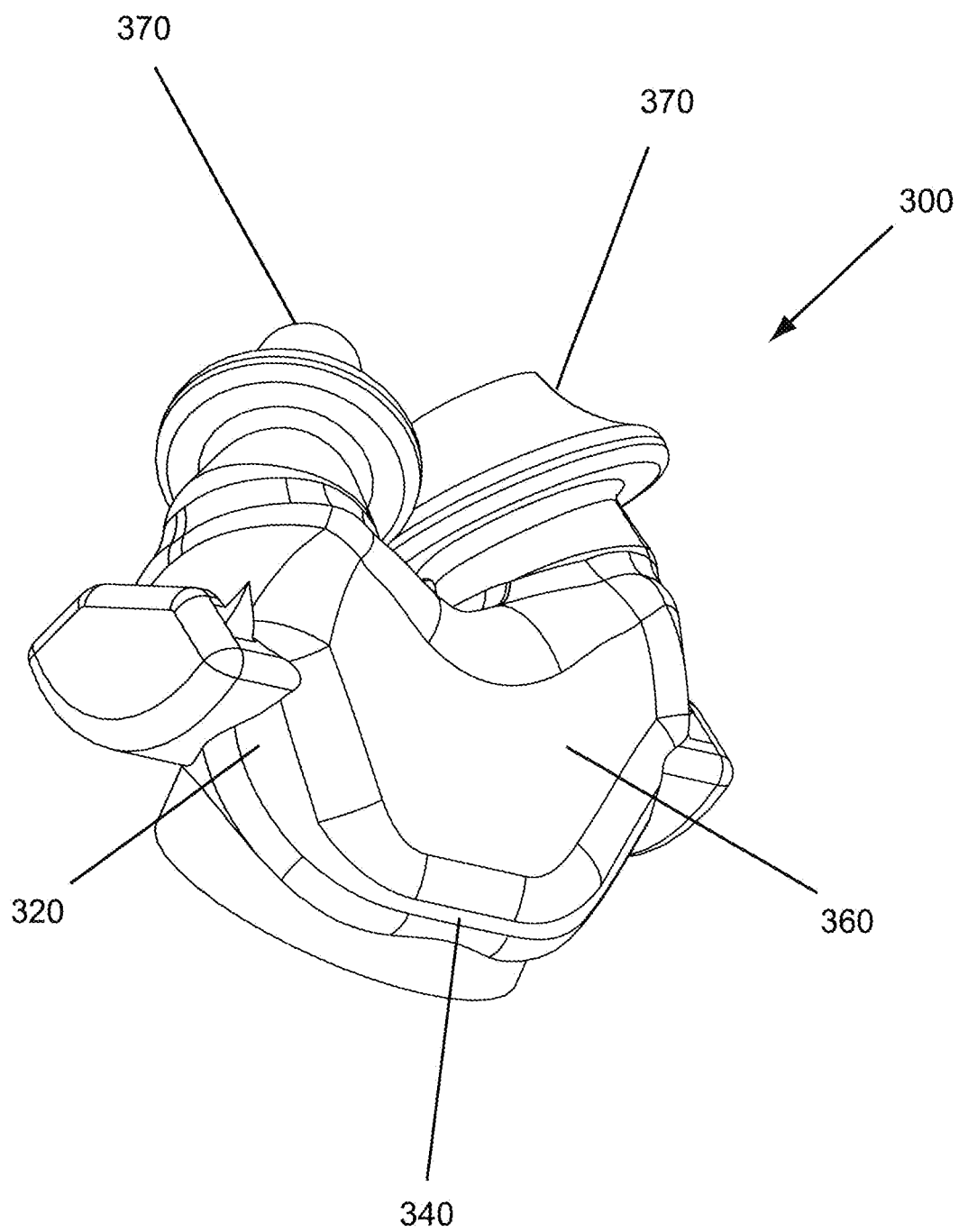
FIG. 3B is a back perspective view of the cannula.

FIGS. 3A and 3B illustrate one preferred form of the cannula 300. While one of ordinary skill in the art will recognize various forms of cannulas sufficient to effectuate a seal with the nares of the patient, the preferred cannula 300 includes a reservoir 310 (best shown in FIG. 4). The reservoir 310 is formed through a first side wall 315, a corresponding second side wall 320, a top wall 330, a corresponding bottom wall 340, a front wall 350, and a back wall 360. However, the reservoir 310 can be of various sizes and shapes—and should not be limited to the orientation herein described. The first side wall 315 is essentially parallel to the second side wall 320 and has essentially the same size and dimension. Positioned on the top wall 330 are one or more nasal prongs 370. The nasal prongs 370 can take many a form as previously discussed and described in greater detail below.

The nasal prongs 370 and various walls 320-360 form one integral single cannula 300. By having an integral cannula, assembly and disassembly are simplified for the patient, the cannula size is reduced and leak between walls and separate cannula parts is eliminated. Although preferably made of a low durometer silicone elastomer, the cannula 300 can be made of plastic, composite or any similar material known to those of ordinary skill in the art.

Referring now to FIG. 3A, located on the front wall 350 of the cannula 300 is an aperture 380. The aperture 380 may be circular and includes an engagement area 381 for fluidically connecting with the ventilation tube 200. The connection may be in the form of a press fit, mating flange, threads, clips, or any connection method known to those of ordinary skill in the art. The engagement area 381 is of sufficient size and dimension to connect and maintain the socket 260 or the connector 270, depending on the embodiment.

The Cannula and Nasal Prongs

Figure 3C:
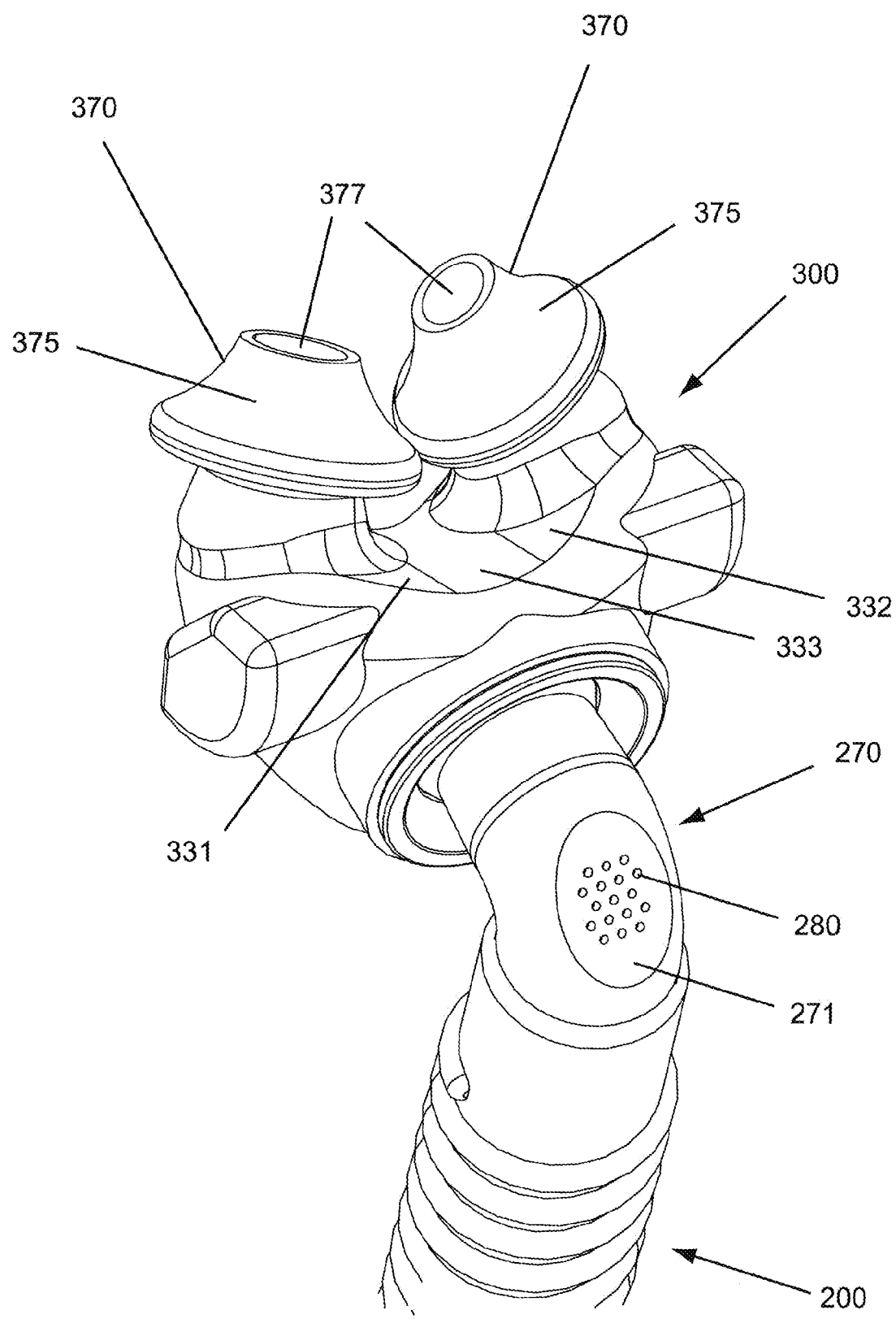
FIG. 3C is a front perspective view of the cannula and the ventilation tube.

FIG. 3C offers a more detailed perspective of the preferred cannula 300. As shown, the top wall 330 of the cannula 300 includes a first portion 331 and a corresponding second portion 332. Positioned between the first portion 331 and second portion 332 is a notch 333. Located on the first portion 330 is a first nasal prong 371. Likewise, a second nasal prong 372 is located on the second portion 332 of the top wall 330. Both nasal prongs 371 and 372 have essentially the same size and dimension. The notch 333 allows for clearance of the bottom of the patient's nose. Further, notch 333 allows the top wall 330 of the cannula 300 to flex inward. The act of inwardly flexing both the first portion 331 and second portion 332 helps orient and position both nasal prongs 370 in relation to the opening of the nares of the patient.

FIG. 3C further shows one general orientation of the nasal prongs 370. Here, the nasal prongs 370 are illustrated as nasal pillow style nasal prongs. As shown, each nasal prong 370 includes a top sealing member 375. The sealing member 375 is essentially elliptical in cross section. At the distal tip of the top sealing member 375 is an opening 377. The opening 377 allows breathable gas to flow from the ventilation tube 200 into the reservoir 310 of the cannula 300 and ultimately to the patient. As illustrated in FIG. 3C, the sealing members 375 of both nasal prongs 370 inwardly tilt toward each other.

In addition, FIG. 3C also shows one orientation for the bleed ports 280 located on the connector 270. In the preferred embodiment, the connector 270 includes an essentially flat portion 271 having one or more bleed ports 280. In one contemplated arrangement, the bleed ports 280 are cloistered and arranged in a plurality of rows having multiple bleed ports 280. The bleed ports 280 are sufficient to allow breathable gas respired from the patient to leave the ventilation interface 100.

Figure 4:
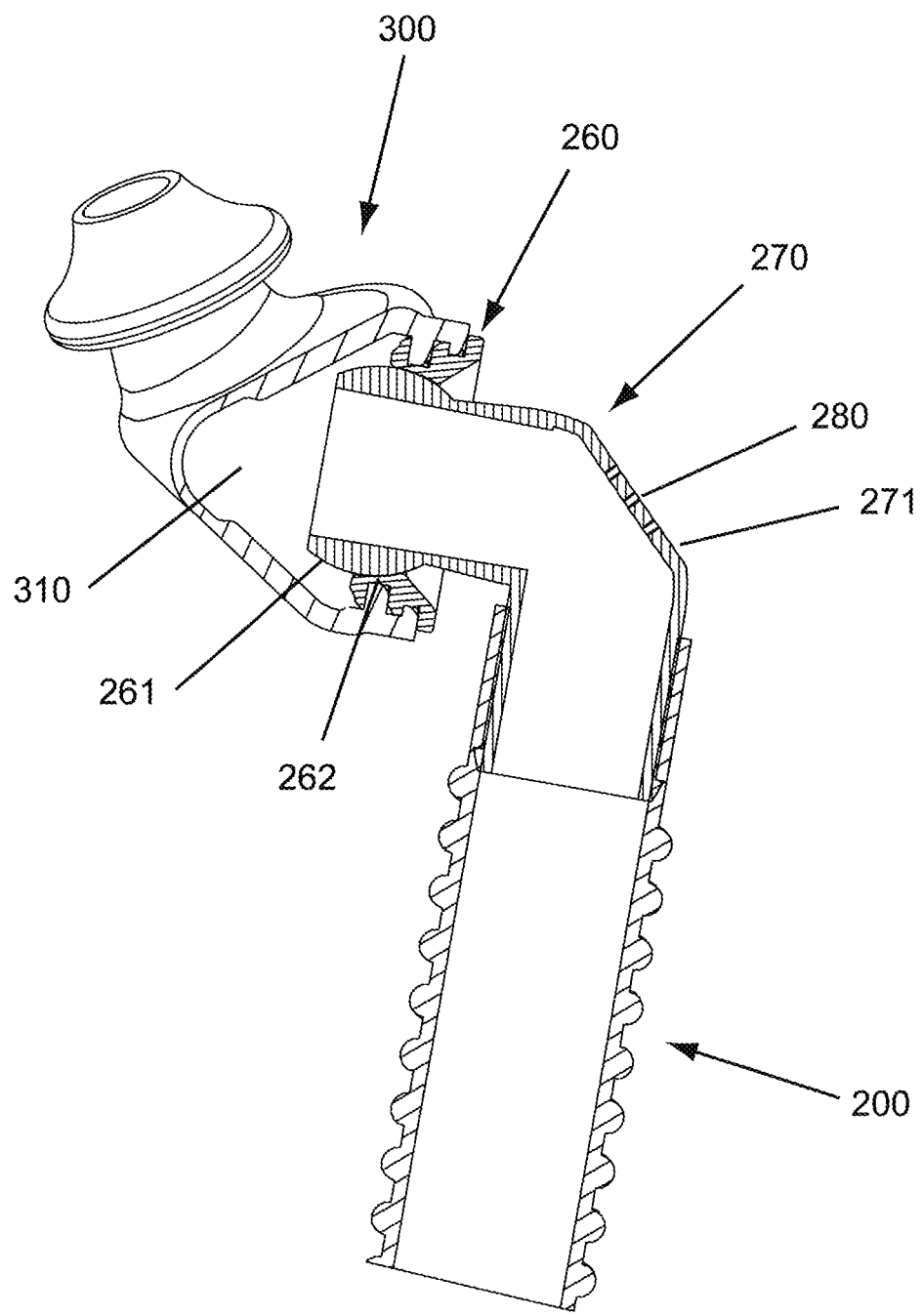
FIG. 4 is a cross-sectional view of the cannula and the ventilation tube.

FIG. 4 offers a cross-sectional view of the cannula 300, the ventilation tube 200, the socket 260 and the connector 270. In addition, FIG. 4 shows how a ball 261 is disposed at one distal end of the connector 270. The ball 261 engages a socket 260. The ball 261 both pivots and rotates within the socket 260 and helps orient the ventilation tube 200.

The Headgear

Figure 5A:
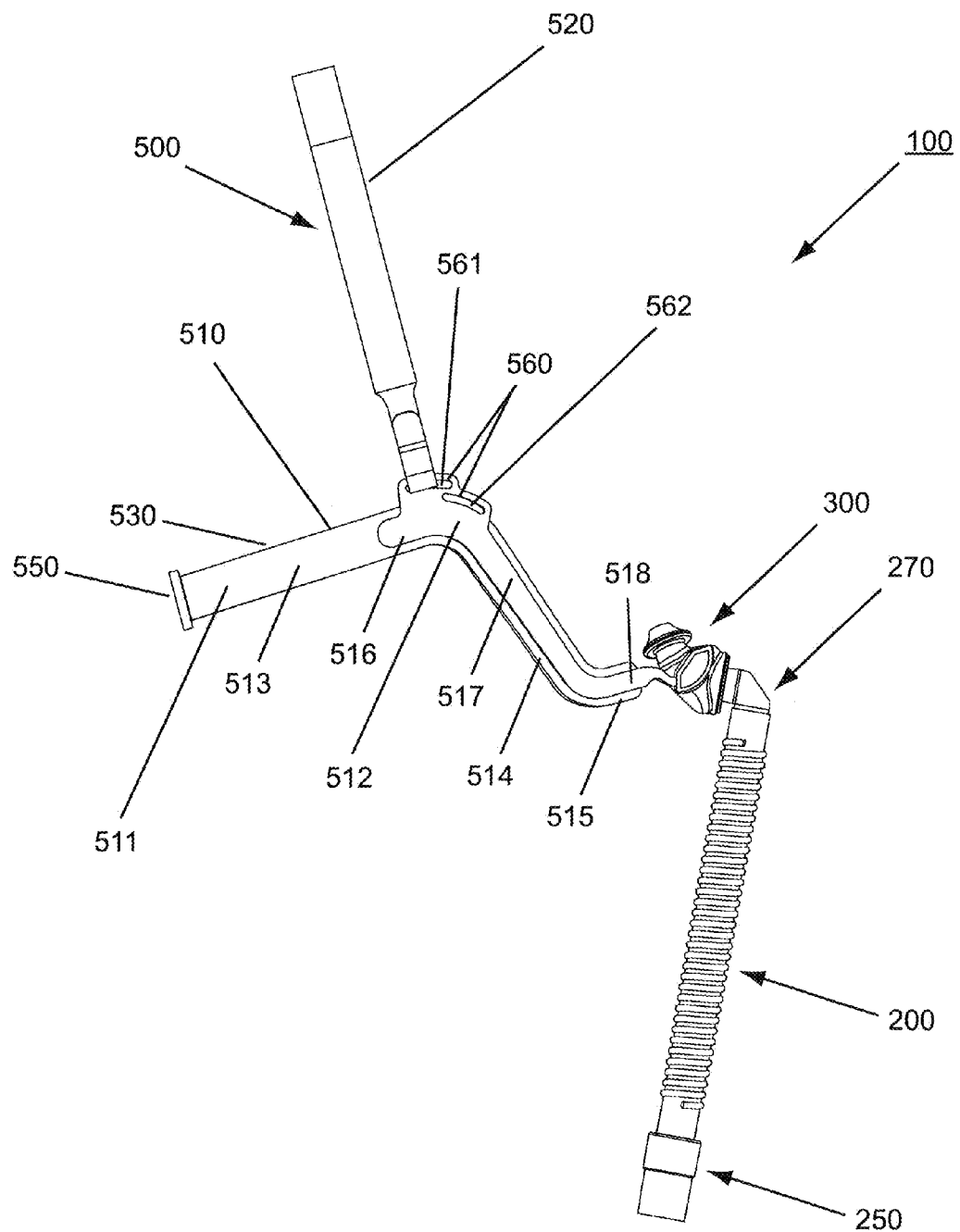
FIG. 5A is a side view of the cannula and headgear assembly.
Figure 5B:
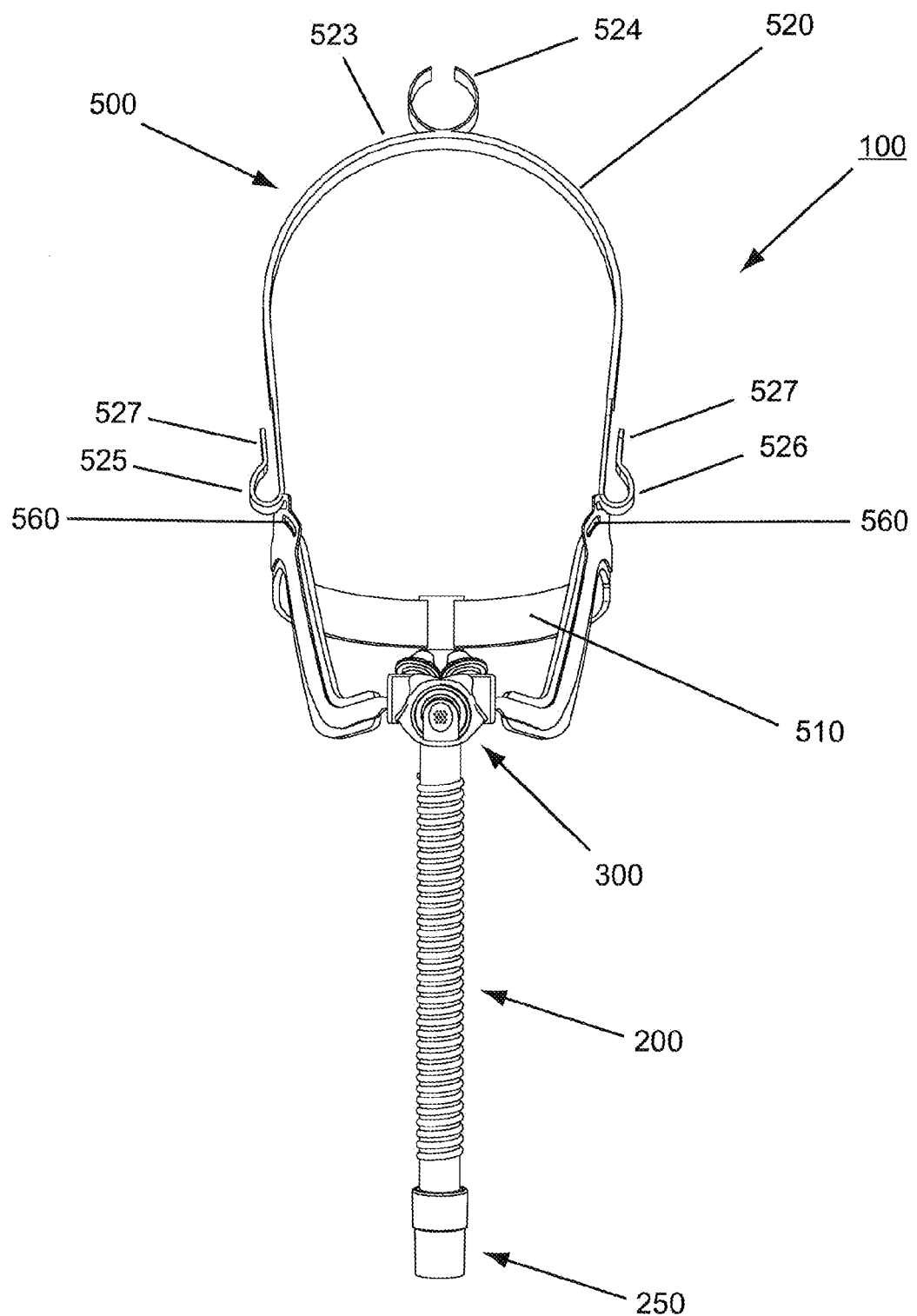
FIG. 5B is a front view of the cannula and headgear assembly.

FIGS. 5A and 5B offer a more detailed view of the preferred headgear 500. FIG. 5A provides a side view of the headgear 500, as well as the cannula 300, connector 270 and the ventilation tube 200. As shown (and previously discussed above), the headgear 500 includes a first strap 510 and a corresponding second strap 520. FIG. 5A illustrates the first portion 530 of the first strap 510, showing both the inner layer 511 and outer layer 512. It is noted that the second portion 540 (shown in FIG. 5B) of the first strap 510 is a mirror image of first portion 530, and therefore has all of the same components and functionality found in the first portion 530.

The inner layer 511 includes three component sections 513-515, each integrally connected to one another at a different angle. These include a first section 513, a second section 514, and a corresponding third section 515. It is preferable that the inner layer 511 is cut from a single piece of material such that all three sections 513-515 are a single piece. During use, the first section 513 is positioned over the back of the head, the second section 514 is positioned between the ear and the eye, and the third section 515 extends towards the cannula 300.

FIG. 5A also shows one preferred structure for the outer layer 512 of the first portion 530. Like the first portion 511, the outer layer 512 may include three outer sections: first outer section 516, second outer section 517, and third outer section 518. These three outer sections 516-518 mirror the orientation of the first section 513, second section 514 and corresponding third section 515 of the first portion 511 described above. Positioned where the first outer section 516 meets the second outer section 517 is at least one slot 560.

As further illustrated in FIG. 5A, preferably there are two slots 560: a first slot 561 and a second slot 562. The first slot 561 is oriented and placed at a different angle in comparison to the second slot 562. This allows the second strap 520 to be attached to either slot 560 at a different orientation so to assist in properly fitting the interface 100 to the patient.

FIG. 5B provides a front view of the interface 100 and illustrates one version of the preferred second strap 520 of the headgear 500. The second strap 520 includes a first end 525 and a corresponding second end 526. In addition, a tube holder 524 is positioned on the middle portion 523 of the second strap 520. The tube holder 524 is capable of maintaining the ventilation tube 200 during use of the interface 100 by the patient.

Positioned at both ends 525 and 526 of the second strap 520 are fasteners 527, which are preferably a hook-and-loop fastener. Each fastener 527 engages a slot 560, located on the first strap 510, sufficient to attach the second strap 520 onto the first strap 510 to form the headgear 500. Moreover, each fastener 527 can be periodically adjusted about either slot 560, including while wearing the interface 100, such that the cannula 300 is properly oriented and sealed in relation to the patient.

The Arced Coupler

FIGS. 6A through 6E provide several embodiments regarding how the headgear 500 is preferably attached to the cannula 300. First turning to FIG. 6A, the cannula 300 includes a first side wall 315 and a corresponding second side wall 320 (best shown and illustrated in FIG. 3B). Positioned on the first side wall 315 is a curved female sleeve 390 and positioned on the corresponding second side wall 320 is a corresponding curved female sleeve 391. It is noted that the curved female sleeves 390 and 391 have all of the same features and functionality. It is also understood that a curved female sleeve could be located on any of the walls of the cannula 300 or even through cannula 300 itself, as long the reservoir 310 remains sealed.

Each curved female sleeve 390 and 391 is capable of receiving and engaging a curved male tine 395 and 396 respectively. Both curved male tines 395 and 396 are located on the third outer sections 518 respectively of the headgear 500. The combination of a curved female sleeve and a curved male tine forms an arced coupler 398 which attaches the headgear 500 onto the cannula 300.

Figure 6A:
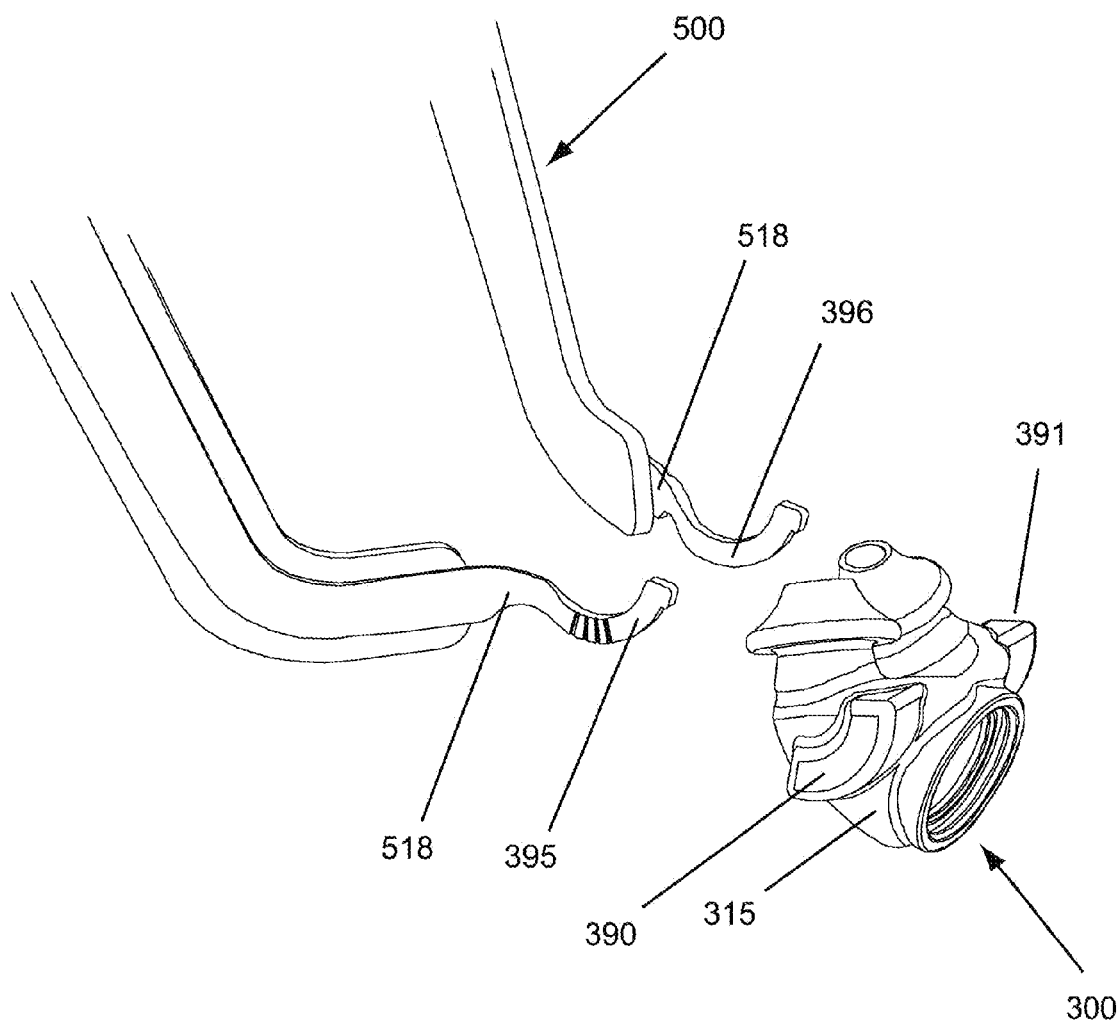
FIG. 6A is a perspective view showing how the headgear connects to two arced couplers located on the cannula.
Figure 6B:
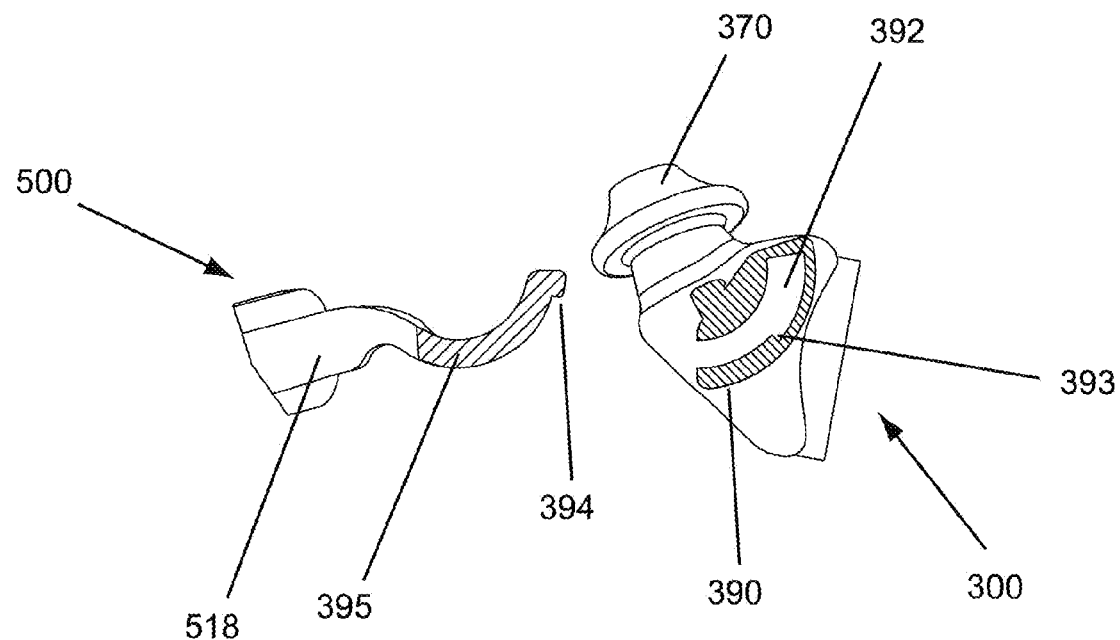
FIG. 6B is a cross-sectional view showing how the headgear connects to the cannula.
Figure 6C:
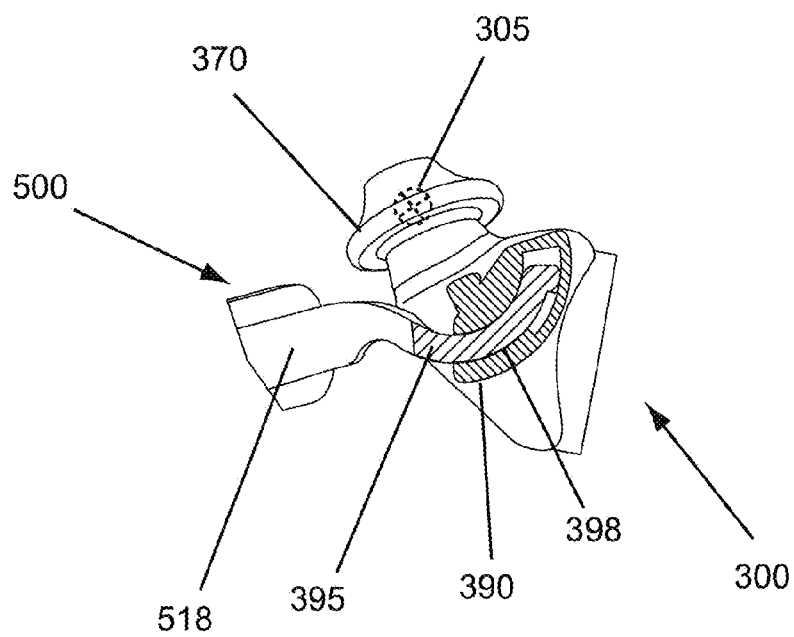
FIG. 6C is a cross-sectional view showing the headgear secured to the cannula.

FIG. 6B illustrates a cross sectional view through curved female sleeve 390 prior to assembly of the curved male tine 395. FIG. 6C illustrates a cross sectional view of an arced coupler 398 (shown in FIG. 6C) (i.e. the curved male tine 395 assembled to the curved female sleeve 390). As is shown in FIG. 6B, curved female sleeve 390 contains a cavity 392 of sufficient size and dimension to engage and secure the curved male tine 395.

As best shown in FIG. 6C, curved male tine 395 can move in an arc path within curved female sleeve 390, allowing cannula 300 to rotate relative to headgear 500 and therefore allow the user to adjust the location of the nasal prongs 370. Also, if the user desires, cannula 300 can be removed from headgear 500 by simply moving cannula 300 further away from the face until curved male tine 395 decouples from curved female sleeve 390.

As opposed to the prior art, this can be done without the user removing the interface from the face. Also as opposed to the prior art, this allows the user to continue to wear the headgear 500 without the cannula 300. Optionally, the distal end of each curved male tine 395 and 396 can include a catch 394. This catch 394 can engage a ledge 393 on the curved female sleeve 390 at one specific angle of rotation to further prevent the incidental removal of the curved male tine 395. If enough force is applied however by the user, the catch 394 can disengage from the ledge 393.

Figure 6D:
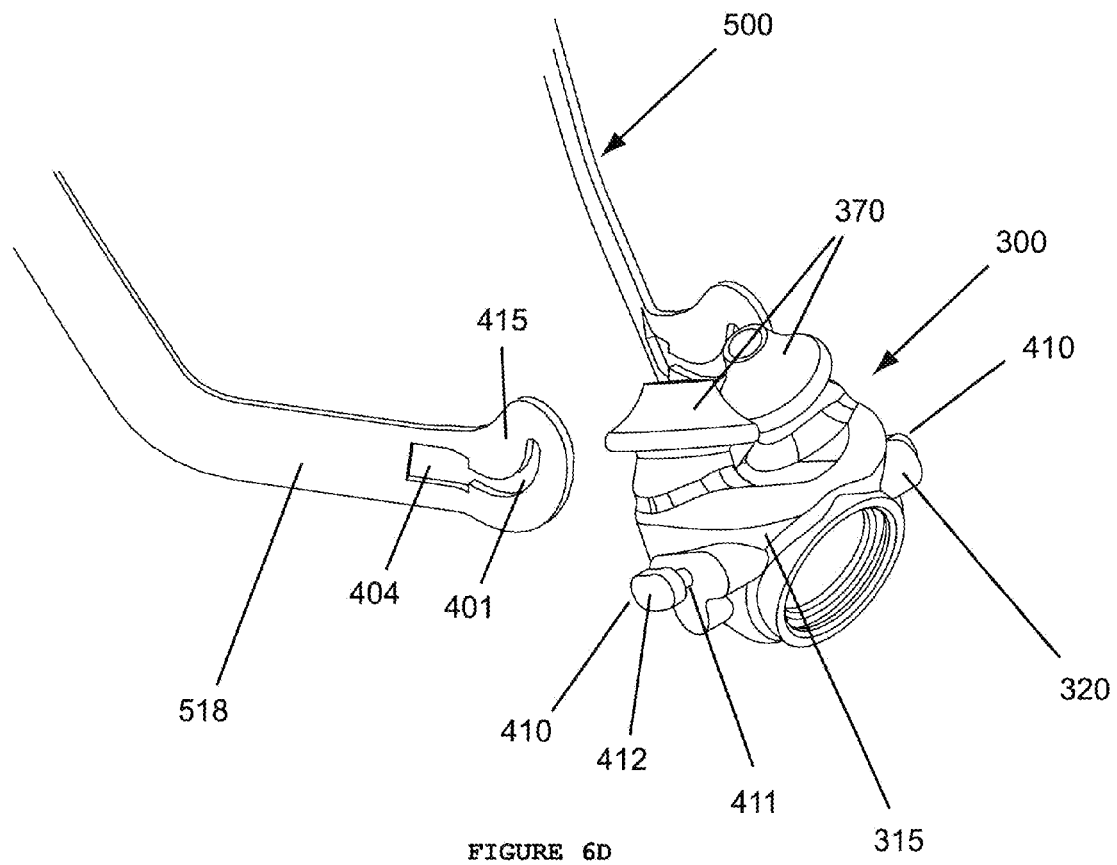
FIG. 6D is a perspective view of an alternative embodiment showing how the headgear connects to the cannula.
Figure 6E:
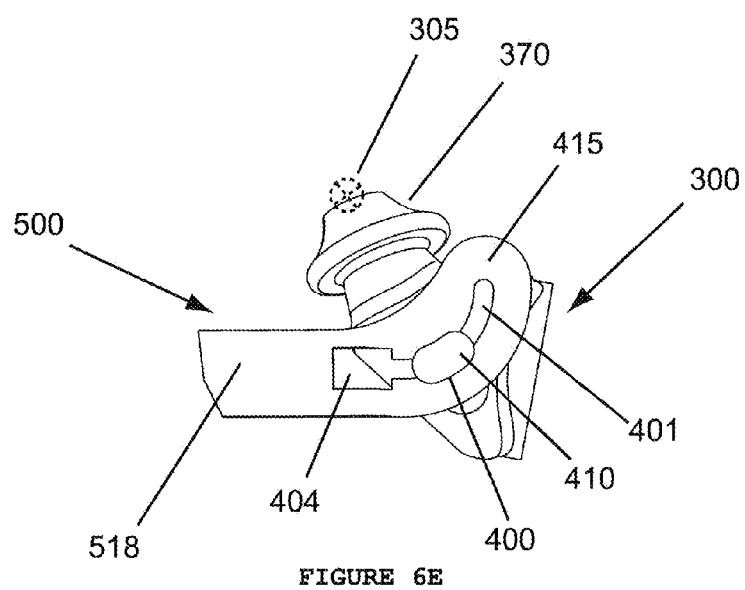
FIG. 6E is a side view of the alternative embodiment showing how the headgear connects to the cannula.

FIG. 6D and FIG. 6E offer a second embodiment of the arced coupler 400. First turning to FIG. 6D, this arced coupler 400 includes a curved female slot 401 located on each of the third outer sections 518 of the headgear 500. Adjacent the curved female slot 401 is a squared opening 404 that is sufficiently larger than the curved female slot 401.

As further shown in FIG. 6D, in this embodiment of the ventilation interface 100, both the first side wall 315 and corresponding second side wall 320 of the cannula 300 include a male member 410. The male member 410 can include stem 411 and a larger head 412. The head 412 of the male member 410 is capable of fitting within the squared opening 404 of the female slot 401 during assembly and disassembly of the headgear 500 from the cannula 300.

Once positioned beyond the squared opening 404, the stem 411 can glide within the curved female slot 401 of the headgear 500, allowing for angular adjustments of the cannula 300 relative to the headgear 500. While the stem 411 is within the curved female slot 401, the head 412 prevents the male member 410 from disengaging from the curved female slot 401 in a direction normal to surface 415 of the headgear 500. Combination of the male member 410 with the curved female slot 401 forms the second embodiment of the arced coupler 400.

One additional optional feature contemplated by the invention is that of an axis for rotational adjustment that passes through or above each nasal prong 370. In an embodiment where the axis passes through the nasal prongs 370, the nasal prongs 370 only rotate and therefore do not change position (i.e., translate and rotate as would occur if the axis were below the nasal prongs 370) relative to the headgear 500 during angular adjustment. This way, an angular adjustment can be made without additional adjustments to the headgear. The embodiments shown in FIGS. 6A to 6E all have an axis 305 that passes through the nasal prongs 370. In these embodiments, the location of the axis 305 is a result of the arced couplers. The location and curvature of the arced couplers 398 or 400 can be modified in design to move the location of the axis 305 so that it passes through or above the nasal prongs 370.

Detachable Nasal Prongs

The invention is further directed towards detachable and adjustable nasal prongs. These alternative nasal prongs are preferably made of a soft, pliable, compressible and biocompatible material such as silicone elastomer. However, one of ordinary skill in the art will recognize other similar materials that can be used. FIG. 3 illustrates nasal prongs 370 that are integral to cannula 300. In these embodiments, the nasal prongs 370 may be detachably coupled with the cannula 300, as is described in detail in the aforementioned referenced patent applications identified above. Detachable nasal prongs may have a different durometer, such as a lower durometer, or be made of a different material than other portions of the cannula.

FIGS. 7A, 7B, 8A, and 8B illustrate two different embodiments for a detachable nasal prong. First turning to FIGS. 7A and 7B, the detachable nasal prong 770 includes a first prong portion 771 and a second prong portion 772. Here, each prong portion is illustrated as a nasal pillow style nasal prong in a non-limiting manner. First prong portion 771 has a first sealing member 775 and second prong portion 772 has a second sealing membrane 776. Depending on which prong portion is oriented towards the patient, one of the first or second sealing members engages the nares. At the tip of first prong portion 771 is a first opening 777 and at the tip of the second prong portion 772 is a second opening 778. Both the first and second openings are capable of providing pressurized breathable gas to the patient.

Located in nasal prong 770 is a ringed member 783, which includes a first ring 784, a recess 785, and a corresponding second ring 786. The ringed member 783 is capable of engaging an aperture 387 (shown in FIG. 9B) located within the first portion 331 and second portion 332 of the cannula 300. Put another way, the ringed member 783 is of a sufficient size and dimension so as to fit and seal within the aperture 387 provided on the top wall 330 of the cannula 300. A connection between the nasal prong 770 and the aperture 387 may be in the form of a press fit, mating flange, threads, clips, or any connection method known to those of ordinary skill in the art.

Figure 7A:
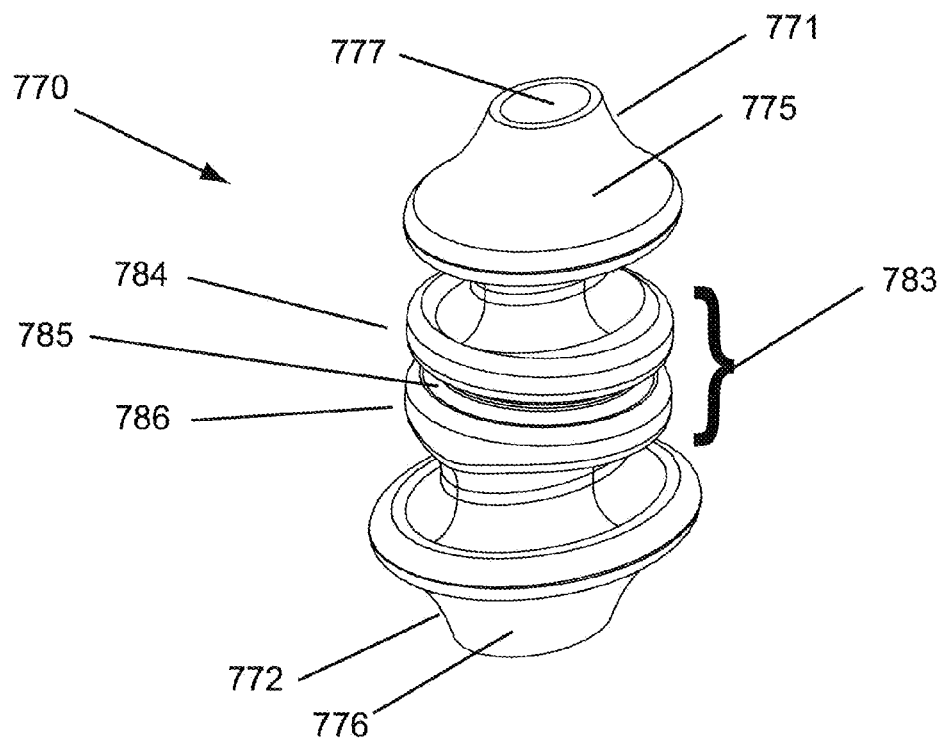
FIG. 7A is a perspective view of a detachable nasal prong.
Figure 7B:
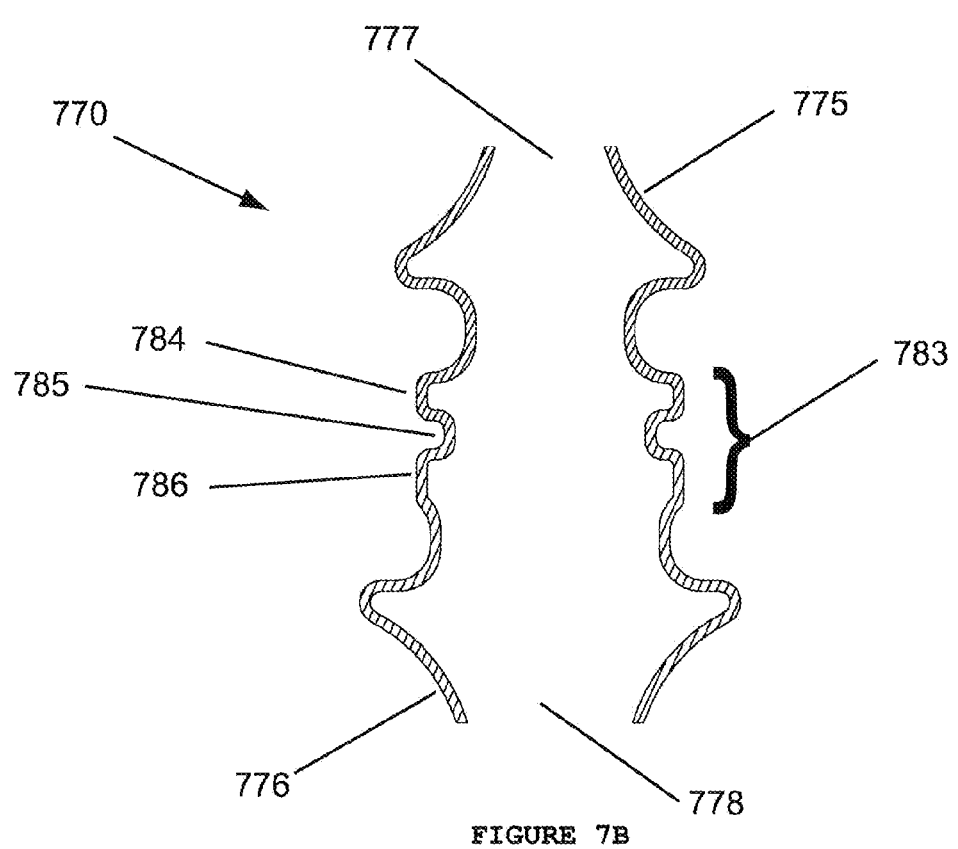
FIG. 7B is a cross-sectional view of the nasal prong shown in FIG. 7A.

FIG. 7B provides a cross sectional view of the detachable nasal prong 770 illustrated in FIG. 7A. Here, the second sealing member 776 is larger in size and dimension in comparison to the first sealing member 775. Likewise, the second opening 778 may be larger than the first opening 777.

The nasal prong 770 illustrated in both FIG. 7A and FIG. 7B further enhances the adjustability of the cannula 300. Should the patient have small nares, the cannula 300 is fitted with nasal prongs 770 such that the first sealing member 775 is oriented to contact the nares, while the second sealing portion 776 is positioned within the cannula 300. Should the patient have large nares, then each nasal prong 770 is turned 180 degrees such that the second sealing member 776 is oriented to contact the nares, while the first sealing portion 775 is positioned within the cannula 300. Should the patient have different sized nares, each nasal prong 770 could be oriented differently to provide the sizing needed to provide a comfortable seal.

Figure 8A:
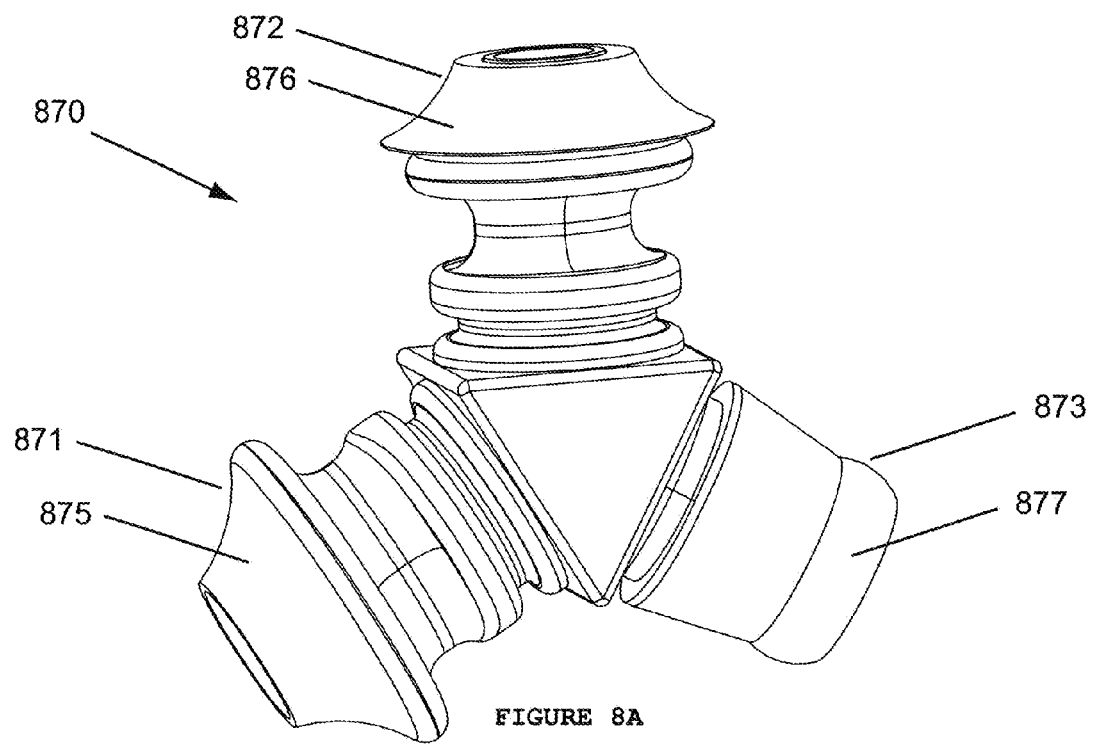
FIG. 8A is a perspective view of another embodiment of a detachable nasal prong.
Figure 8B:
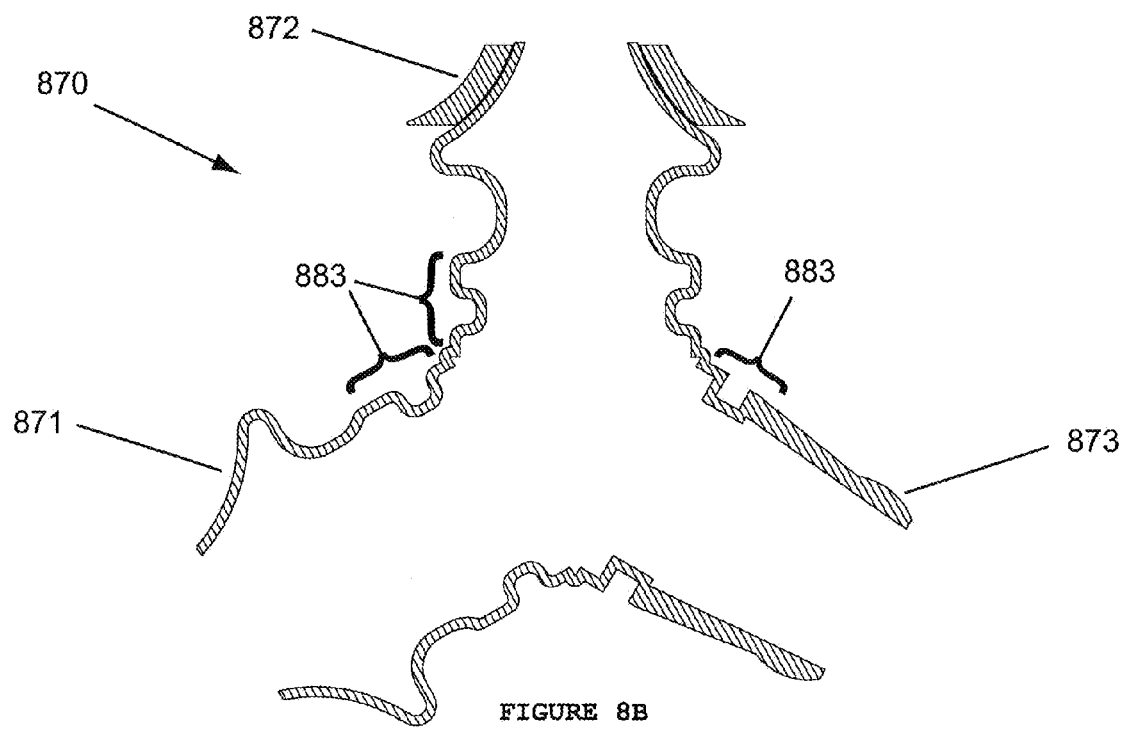
FIG. 8B is a cross-sectional view of the nasal prong shown in FIG. 8A.

FIGS. 8A and 8B show another similar embodiment of a detachable nasal prong. The detachable nasal prong 870 includes a first prong portion 871, a second prong portion 872, and a third prong portion 873. This embodiment illustrates that more than two nasal portions can be located on a detachable nasal prong 870. This embodiment also illustrates that each nasal prong portion can be of a different size, or even of a different type of nasal prong. For example, first prong portion 871 can be a nasal pillow style nasal prong, the second prong portion 872 can be a nasal pillow style nasal prong that is smaller than the first prong portion 871, and the third prong portion 873 can be a nasal insert style nasal prong. First prong portion 871 has a first sealing surface 875, and third prong portion 873 has a third sealing surface 877. Second prong portion 872 may have a seal component 876 that is coupled to it. Seal component 876 may be a different durometer or material than second prong portion 872. For example, second prong portion 872 may be silicone and seal component 876 may be constructed of foam or gel.

Figure 9A:
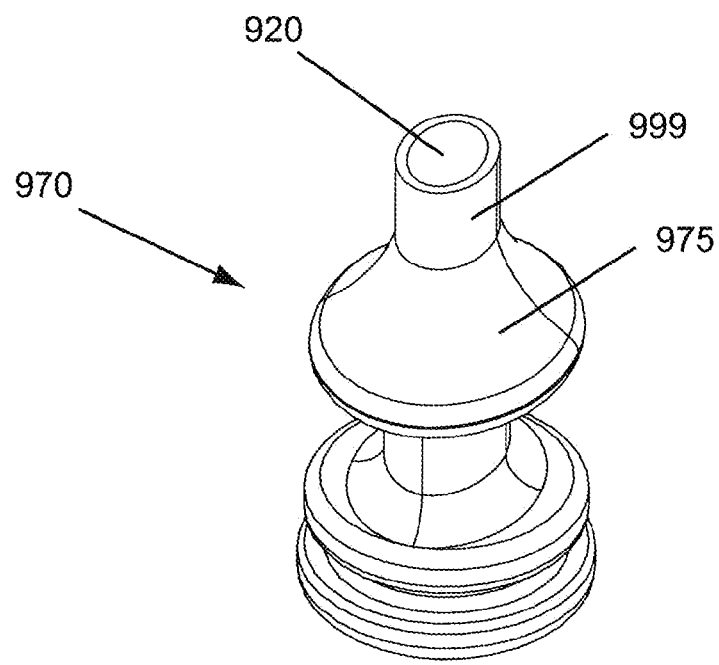
FIG. 9A is a perspective view of an alternative embodiment of a nasal prong.
Figure 9B:
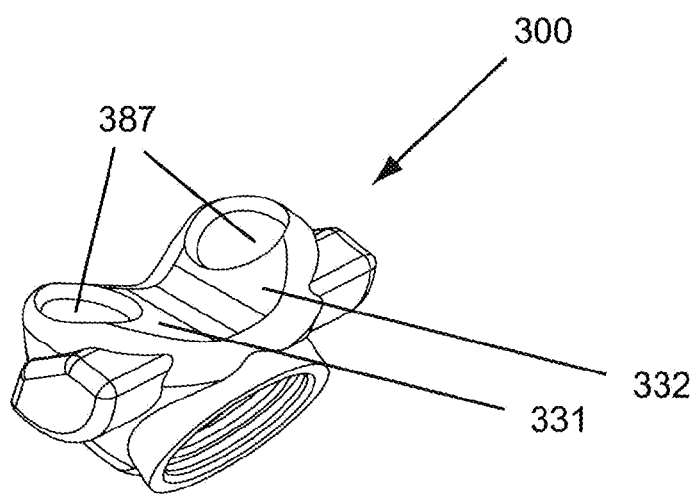
FIG. 9B is a perspective view of the cannula configured to interface with detachable nasal prongs.

Similar to nasal prong 770, each prong portion of nasal prong 870 has a ringed member 883, which is capable of engaging an aperture 387 located within the first portion 331 and second portion 332 of the cannula 300 (all shown in FIG. 9B). Depending on which prong portion is positioned towards the patient, one of the first, second, or third prong portions engages the nares while the other two remaining prong portions would be within the cannula 300. Detachable nasal prongs 770 and 870 could also be adapted to couple with any mask that has nasal prongs, including hybrid masks (i.e., those masks that combine masks such as having an oral cavity with nasal prongs).

FIGS. 9A, 10A, 10B, and 10C offer additional structure that can be applied to a nasal prong, such as the integral nasal prong 370 or the detachable nasal prong 770. FIG. 9A illustrates a nasal prong 970, which is shown to be detachable in a non-limiting way. The sealing member 975 includes an upper portion 999, which is located at the distal tip of the nasal prong 970 and which has an opening 920. The upper portion 999 may be adjustable.

Figure 10A:
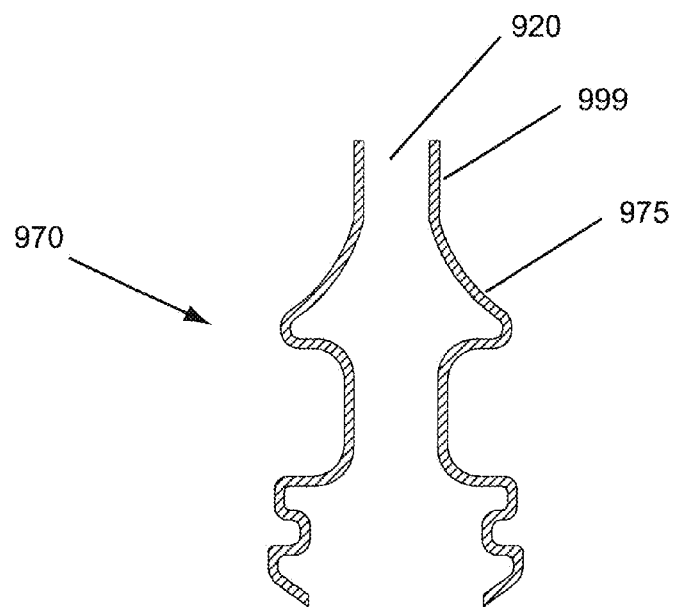
FIG. 10A is a cross-sectional view of one configuration of the alternative nasal prong embodiment shown in FIG. 9A.
Figure 10B:
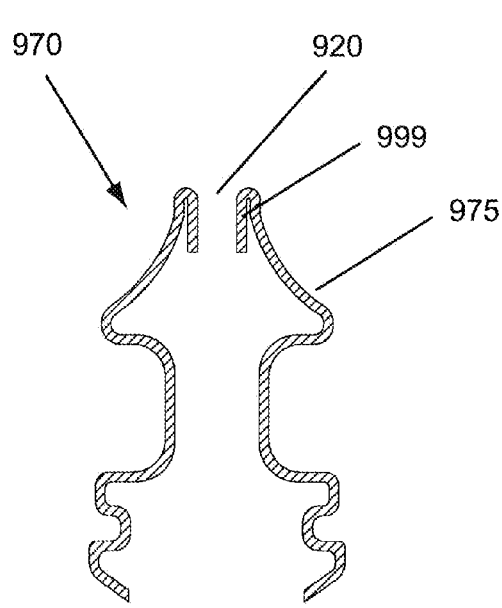
FIG. 10B is a cross-sectional view of a second configuration of the alternative nasal prong embodiment shown in FIG. 9A.
Figure 10C:
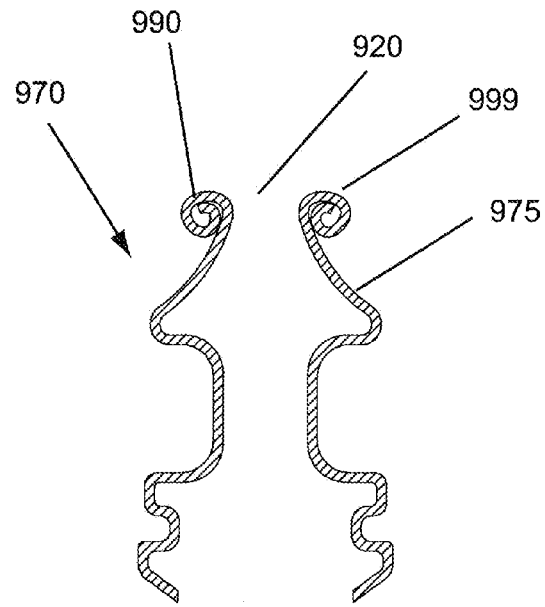
FIG. 10C is a cross-sectional view of a third configuration of the nasal prong embodiment shown in FIG. 9A.

FIGS. 10A, 10B, and 10C illustrate cross-sections of different configuration of the nasal prong 970. In FIG. 10A, upper portion 999 is shown adjusted to be fully extended. In this configuration, the upper portion 999 extends further into the nose of the patient during use. In this configuration, the upper portion 999 serves several purposes. First the upper portion 999 minimizes the opportunity for the nasal prong 970 to inadvertently become dislodged from the patient's nose. Second, the upper portion 999 helps the flow of the breathable gas become laminar in order to improve patient comfort.

Upper portion 999 could also fold or roll inwardly. This adjustment could shorten the length of the upper portion 999, could decrease the size of the opening 920, or could change the size or shape of the sealing member 975. FIG. 10B illustrates one example of an embodiment where the upper portion 999 has been folded inwardly. Upper portion 999 could also fold or roll outwardly. This adjustment could shorten the length of the upper portion 999, could increase the size of the opening 920, or could change the size or shape of the sealing member 975. FIG. 10C illustrates one example of an embodiment where the upper portion 999 has been rolled outwardly. A rolled or folded upper portion 999 could also serve to create a sealing bead 990, as shown in FIG. 10C. Further adjustment of the upper portion 999 would further adjust the size and shape of the sealing bead 990.

Figure 11A:
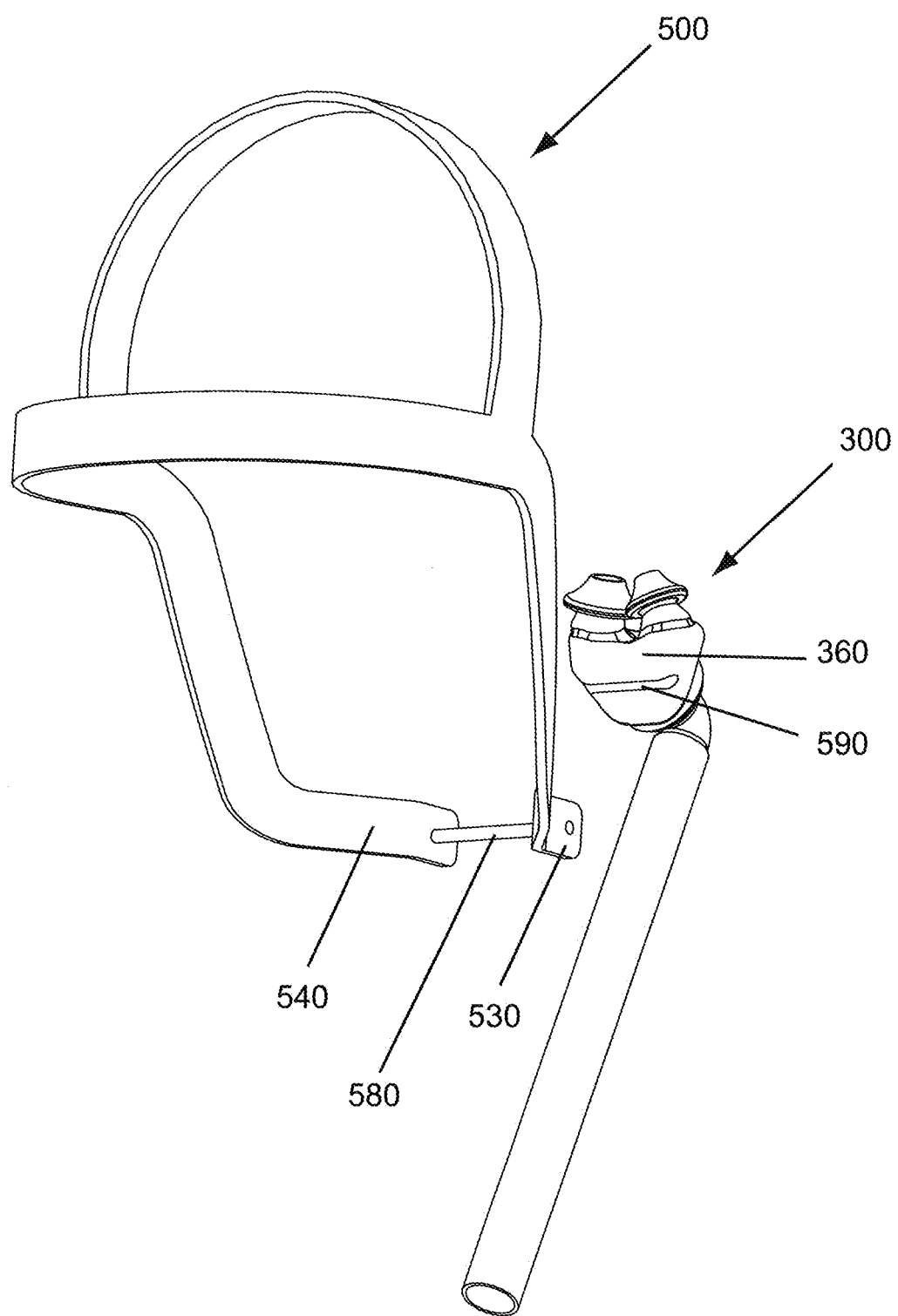
FIG. 11A is a perspective view of an alternative embodiment showing how the headgear connects to the cannula.
Figure 11B:
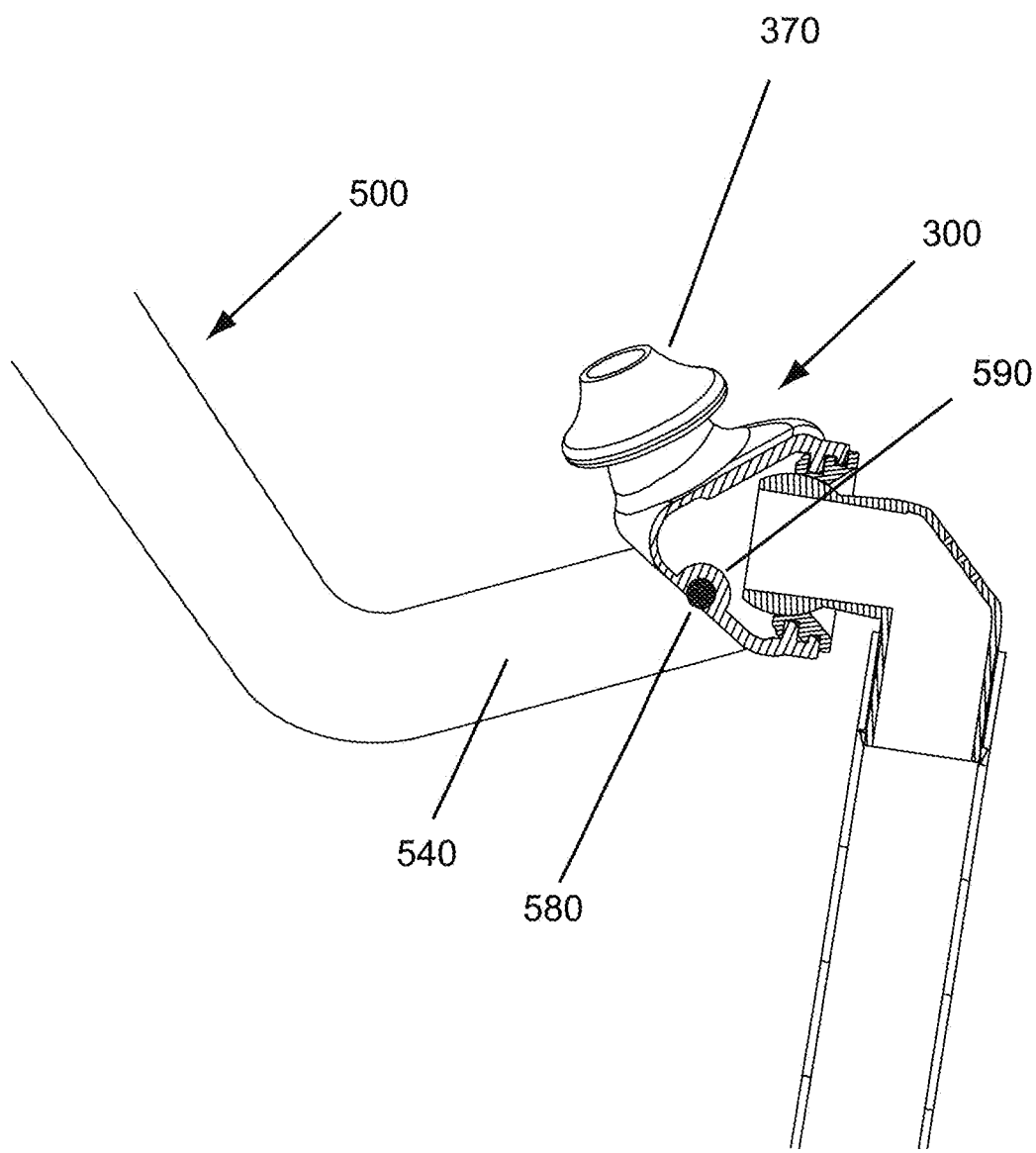
FIG. 11B is a cross-sectional view of the alternative embodiment shown in FIG. 11A.

FIGS. 11A and 11B illustrate another embodiment regarding how the headgear 500 is attached to the cannula 300. FIG. 11A shows the cannula 300 disassembled from the headgear 500. In this embodiment, cannula 300 has back wall 360 that contains a receptacle 590, and headgear 500 has a pin 580 that is located between the first portion 530 and the second portion 540. In embodiments, receptacle 590 could be located on any portion of the cannula 300 and could be embedded within or protrude from cannula 300. Pin 580 is configured to fit into receptacle 590 and provides for easy assembly and disassembly of the cannula 300 from the headgear 500. For example, the user could remove the cannula 300 while still wearing the headgear 500.

FIG. 11B is a cross-section of the embodiment when assembled. Pin 580 is configured to allow the user to make angular adjustments to the cannula 300 with respect to the headgear 500 for improved fitting and comfort. Pin 580 is preferably made of a harder material than cannula 300 and could be pushed into the receptacle 590 during assembly. Pin 580 is preferably circular in cross-section to allow for rotation with respect to the receptacle 590. The friction fit between the pin 580 and the receptacle 590 would allow the user to place the cannula 300 in an infinite number of angular positions.

The pin 580 could have an alternate cross-sectional shape or have details to allow the cannula to rotate to a predetermined number of positions. For example, the pin 580 could be egg shaped, square, hex shaped, or any other shape. The pin 580 could have divots, slots, bumps, ratchets, cams, or other types of details. The receptacle 590 may have a corresponding shape or details to engage the pin 580. The shapes and details described for the pin 580 could be applied to the receptacle 590 instead and the details of the receptacle 590 could be applied to the pin 580 instead, as would be recognized by those having ordinary skill in the art. In embodiments, a secondary part (not shown), such as a bushing, could be located between the pin 580 and the receptacle 590.

Preferably, the pin 580 is fixed to the headgear 500 and the cannula 300 rotates about pin 580. In an alternate configuration, the pin 580 could be assembled to the headgear 500 in a manner that allowed it to rotate within the headgear. For example, the pin 580 could fit into holes (not shown) in the headgear 500. Either configuration ultimately allows the user to rotate the cannula 300 with respect to the headgear 500. In this alternate configuration, it is understood that the methods and details described above pertaining to the pin 580, the receptacle 590, and their connection could be applied to the pin 580, the holes (not shown) in the headgear, and their connection.

Figure 12:
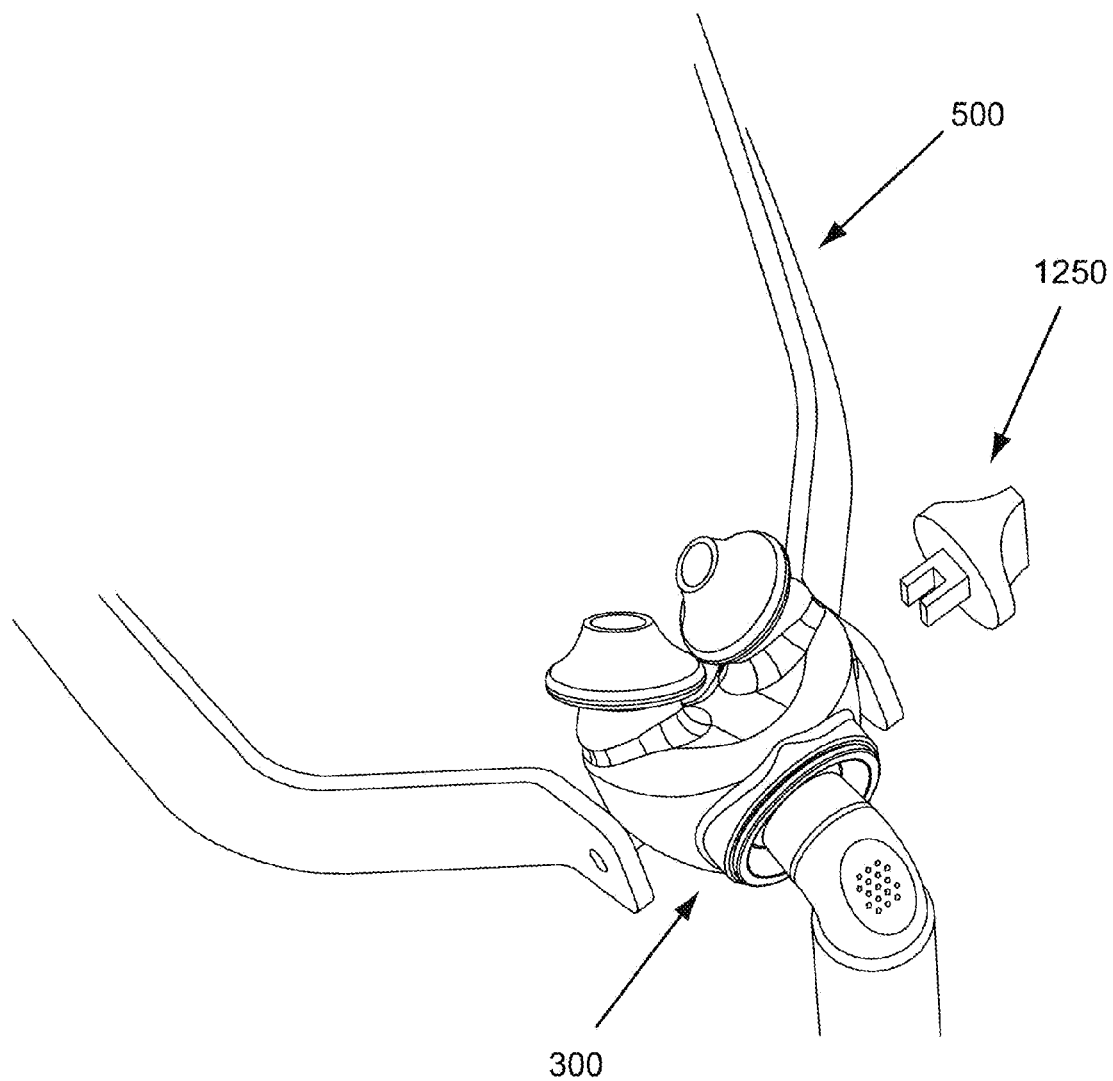
FIG. 12 is a perspective view of a handle applied to a cannula and headgear assembly.

FIG. 12 illustrates a handle 1250, which could be utilized on embodiments to assist in rotating the cannula 300. The handle 1250 provides the user with additional leverage and an easier feature to grasp to facilitate fitting or calibration. The handle 1250 could also function as a key, allowing the cannula 300 to only move relative to the headgear 500 if the handle 1250 is engaged. The handle 1250 could be engaged by insertion, twisting, by pressing or releasing a button, or any other method recognized by those having ordinary skill in the art. A handle 1250 that is detachable is preferred so it could be constructed in any manner, out of any material, or any size that provided the most leverage. While the handle 1250 could be integral, a detachable handle 1250 could be removed prior to the patient lying down as to not interfere with the comfort of using the interface.

Figure 13:
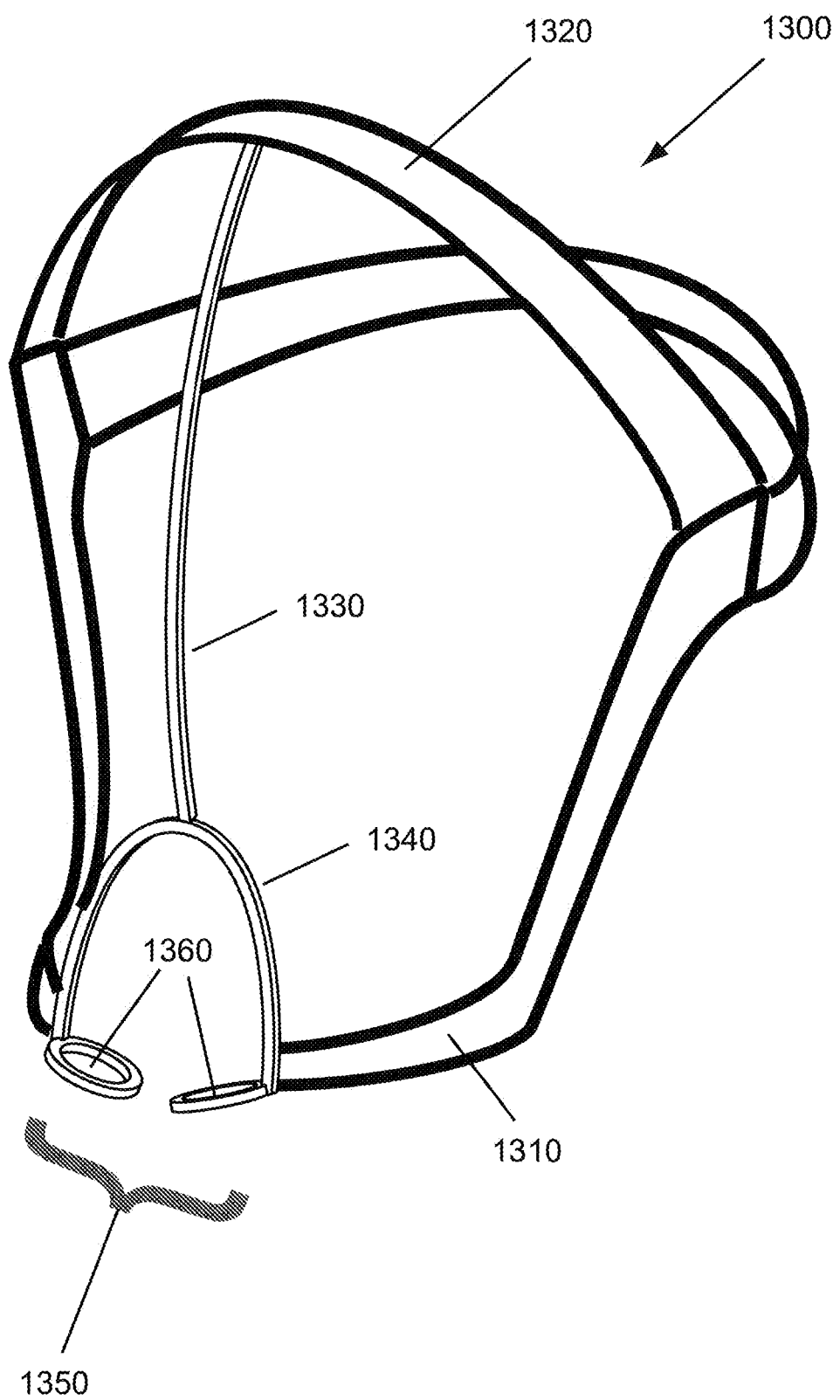
FIG. 13 is a perspective view of yet another embodiment of the headgear.

FIG. 13 shows yet another embodiment of a headgear for the ventilation interface. Headgear 1300 has a first strap 1310 and a second strap 1320. Headgear 1300 also has a center strap 1330 that connects to the second strap 1320. Center strap 1330 has a nose portion 1340, which goes over at least a portion of the nose. At the base of the nose portion 1340 is a connecting portion 1350. Connecting portion 1350 is configured to couple with the ventilation interface. Connecting portion 1350 has at least one aperture 1360 that could engage with the nasal cannula 300 or directly with the nasal prongs 370. By tightening any of the first strap 1310, the second strap 1320, or the center strap 1330, the nasal prongs would engage with nares of the patient to create a comfortable seal. This tightening would create an upward sealing force on nares from the nasal prongs.

The connecting portion 1350 could be configured to couple with other types of mask seals, such as facial cushions, and allow for the patient to create a comfortable seal with the face. Similar to the materials of the headgear 500, the materials of headgear 1300 are preferably soft and flexible, such as the fabrics discussed previously. Polymers, such as silicone or rubber, could also be utilized in the headgear 1300. Nose portion 1340 is preferably made of silicone.

We claim:

1. A ventilation interface, comprising:
a cannula having a top wall and first and second side walls and at least one female sleeve on the first side wall traversing a female curve between an entrance end and a terminal end thereof;
at least one nasal prong, each nasal prong attached to the top wall of the cannula;
a ventilation tube operable with the cannula for providing pressurized breathable gas to a patient; and
headgear having at least one male tine traversing a male curve between proximal and distal ends, wherein the distal end of the at least one male tine is slidably insertable into the entrance end of the at least one female sleeve such that more of the male curve is received within the female curve as the distal end of the male tine approaches the terminal end of the female sleeve;
wherein an angle of the at least one nasal prong relative to the headgear is varied about an axis defined by the male and female curve as the distal end of the male tine approaches the terminal end of the female sleeve.

2. The ventilation interface of claim 1, wherein the cannula further includes a front wall, a back wall and a bottom wall, which when combined with the top wall form a reservoir.

3. The ventilation interface of claim 1, wherein the top wall of the cannula includes a notch for providing inward flexibility of the top wall to position the at least one nasal prong relative to the nares of the patient.

4. The ventilation interface of claim 1, wherein the at least one female sleeve comprises two curved female sleeves and the at least one male time comprises two corresponding curved male tines operable to rotatably secure the cannula to the headgear.

5. The ventilation interface of claim 4, wherein one of the two curved female sleeves is located on the second side wall of the cannula.

6. The ventilation interface of claim 1, wherein the ventilation interface includes at least one bleed port.

7. The ventilation interface of claim 1, wherein the ventilation tube attaches to the cannula through a connector.

8. The ventilation interface of claim 7, wherein the connector is a ball-and-socket connector.

9. The ventilation interface of claim 1, wherein each nasal prong is removably attached to the top wall of the cannula.

10. The ventilation interface of claim 9, wherein each nasal prong has at least one sealing portion.

11. The ventilation interface of claim 9, wherein each nasal prong has a first sealing portion and a second sealing portion, wherein the nasal prong is structured such that each of the first sealing portion and the second sealing portion are of different sizes and can be reversibly attached to the top wall of the cannula such that one of the first or second sealing portions is positioned within the cannula while the other is positioned exteriorly of the top wall of the cannula.

12. The ventilation interface of claim 1, wherein each nasal prong has an adjustable upper portion with an opening located at a distal tip of the nasal prong.

13. A ventilation interface, comprising:
a cannula having a top wall and two side walls and at least one female sleeve on one of the two side walls traversing a female curve between an entrance end and a terminal end thereof;
at least one nasal prong, each nasal prong attached to the top wall of the cannula;

a ventilation tube operable with the cannula for providing pressurized breathable gas to a patient; and headgear having at least one male tine traversing a male curve between proximal and distal ends, wherein the distal end of the at least one male tine is slidably insertable into the entrance end of the at least one female sleeve such that more of the male curve is received within the female curve as the distal end of the male tine approaches the terminal end of the female sleeve, wherein the cannula can rotate relative to the headgear about an axis that is located either through the nasal prong or above the nasal prong to allow adjustment of the location of the at least one nasal prong;

wherein the rotation of the cannula relative to the headgear about the axis is accomplished by varying an insertion depth of the male curve into the female curve.

14. A ventilation interface, comprising:

a cannula having a nasal prong attached to a top wall thereof and having at least one female sleeve on one of two side walls thereof traversing a female curve between an entrance end and a terminal end thereof;

a ventilation tube for providing pressurized breathable gas to a patient;

a ball and socket connector attached between the ventilation tube and the cannula, the ball-and-socket connector allowing the ventilation tube to both swivel and rotate; and headgear having at least one male tine traversing a male curve between proximal and distal ends, wherein the distal end of the at least one male tine is slidably insertable into the entrance end of the at least one female sleeve such that more of the male curve is received within the female curve as the distal end of the male tine approaches the terminal end of the female sleeve;

wherein an angle of the at least one nasal prong relative to the headgear is varied about an axis defined by the male and female curve as the distal end of the male tine approaches the terminal end of the female sleeve.

* * * * *